United States Patent
Hegeman et al.

(10) Patent No.: US 9,737,365 B2
(45) Date of Patent: Aug. 22, 2017

(54) TOOL WITH ARTICULATION LOCK

(71) Applicant: Intuitive Surgical Operations, Inc., Sunnyvale, CA (US)

(72) Inventors: David Elias Hegeman, San Jose, CA (US); David J. Danitz, San Jose, CA (US); Cameron D. Hinman, Thurmond, NC (US); Lincoln J. Alvord, Redwood City, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 14/735,564

(22) Filed: Jun. 10, 2015

(65) Prior Publication Data

US 2015/0351854 A1 Dec. 10, 2015

Related U.S. Application Data

(60) Continuation of application No. 13/334,628, filed on Dec. 22, 2011, now Pat. No. 9,072,427, which is a
(Continued)

(51) Int. Cl.
*A61B 1/00* (2006.01)
*A61B 19/00* (2006.01)
(Continued)

(52) U.S. Cl.
CPC ........ *A61B 19/22* (2013.01); *A61B 17/00234* (2013.01); *A61B 17/29* (2013.01);
(Continued)

(58) Field of Classification Search
USPC ................................. 600/139, 141–142, 148
See application file for complete search history.

(56) References Cited

U.S. PATENT DOCUMENTS

| 1,820,463 A | 8/1931 | Klein |
| 3,060,972 A | 10/1962 | Sheldon |

(Continued)

FOREIGN PATENT DOCUMENTS

| EP | 165718 A2 | 12/1985 |
| EP | 0598618 A2 | 5/1994 |

(Continued)

OTHER PUBLICATIONS

International Preliminary Report on Patentability dated Jun. 24, 2014 for PCT Application No. PCT/FI2012/051262.
(Continued)

*Primary Examiner* — Matthew J Kasztejna

(57) ABSTRACT

The invention provides surgical or diagnostic tools and associated methods that offer user control for operating remotely within regions of the body. These tools include a proximally-located actuator for the operation of a distal end effector, as well as proximally-located actuators for articulational and rotational movements of the end effector. Control mechanisms and methods refine operator control of end effector actuation and of these articulational and rotational movements. An articulation lock allows the fixing and releasing of both neutral and articulated configurations of the tool and of consequent placement of the end effector. The tool may also include other features. A multi-state ratchet for end effector actuation provides enablement-disablement options with tactile feedback. A force limiter mechanism protects the end effector and manipulated objects from the harm of potentially excessive force applied by the operator. A rotation lock provides for enablement and disablement of rotatability of the end effector.

17 Claims, 30 Drawing Sheets

Related U.S. Application Data division of application No. 11/787,543, filed on Apr. 16, 2007, now Pat. No. 8,100,824, which is a continuation-in-part of application No. 11/181,445, filed on Jul. 13, 2005, now Pat. No. 7,615,066, which is a continuation of application No. 10/444,769, filed on May 23, 2003, now Pat. No. 7,090,637, and application No. 11/787,543, which is a continuation-in-part of application No. 11/121,668, filed on May 3, 2005, now Pat. No. 8,182,417.

(60) Provisional application No. 60/630,912, filed on Nov. 24, 2004.

(51) Int. Cl.
   *H04M 1/725* (2006.01)
   *A61B 17/00* (2006.01)
   *A61B 17/32* (2006.01)
   *A61B 17/29* (2006.01)
   *H04B 7/212* (2006.01)
   *H04W 24/08* (2009.01)
   *A61B 34/00* (2016.01)

(52) U.S. Cl.
   CPC ...... *A61B 17/320016* (2013.01); *A61B 34/70* (2016.02); *A61B 34/71* (2016.02); *H04B 7/2125* (2013.01); *H04M 1/72519* (2013.01); *H04W 24/08* (2013.01); *A61B 2017/0042* (2013.01); *A61B 2017/0046* (2013.01); *A61B 2017/00367* (2013.01)

(56) References Cited

U.S. PATENT DOCUMENTS

| | | |
|---|---|---|
| 3,071,161 A | 1/1963 | Ulrich |
| 3,190,286 A | 6/1965 | Stokes |
| 3,557,780 A | 1/1971 | Sato |
| 3,605,725 A | 9/1971 | Bentov |
| 4,246,661 A | 1/1981 | Pinson |
| 4,302,138 A | 11/1981 | Zarudiansky |
| 4,346,470 A | 8/1982 | Alvarez, III et al. |
| 4,466,649 A | 8/1984 | Ozawa |
| 4,489,826 A | 12/1984 | Dubson |
| 4,551,061 A | 11/1985 | Olenick |
| 4,566,843 A | 1/1986 | Iwatsuka et al. |
| 4,580,551 A | 4/1986 | Siegmund et al. |
| 4,700,693 A | 10/1987 | Lia et al. |
| 4,763,669 A | 8/1988 | Jaeger |
| 4,790,294 A | 12/1988 | Allred, III et al. |
| 4,834,761 A | 5/1989 | Walters |
| 4,838,859 A | 6/1989 | Strassmann |
| 4,854,626 A | 8/1989 | Duke |
| 4,873,965 A | 10/1989 | Danieli |
| 4,880,015 A | 11/1989 | Nierman |
| 4,921,293 A | 5/1990 | Ruoff et al. |
| 4,984,951 A | 1/1991 | Jameson |
| 5,143,505 A | 9/1992 | Burdea et al. |
| 5,158,086 A | 10/1992 | Brown et al. |
| 5,174,276 A | 12/1992 | Crockard |
| 5,209,747 A | 5/1993 | Knoepfler |
| 5,251,611 A | 10/1993 | Zehel et al. |
| 5,257,618 A | 11/1993 | Kondo |
| 5,271,381 A | 12/1993 | Ailinger et al. |
| 5,273,026 A | 12/1993 | Wilk |
| 5,286,228 A | 2/1994 | Lee et al. |
| 5,297,443 A | 3/1994 | Wentz |
| 5,314,424 A | 5/1994 | Nicholas |
| 5,322,064 A | 6/1994 | Lundquist |
| 5,325,845 A | 7/1994 | Adair |
| 5,330,502 A | 7/1994 | Hassler et al. |
| 5,354,162 A | 10/1994 | Burdea et al. |
| 5,373,747 A | 12/1994 | Ogawa et al. |
| 5,381,782 A | 1/1995 | DeLaRama et al. |
| 5,403,342 A | 4/1995 | Tovey et al. |
| 5,405,344 A | 4/1995 | Williamson et al. |
| 5,425,743 A | 6/1995 | Nicholas |
| 5,441,494 A | 8/1995 | Ortiz |
| 5,454,827 A | 10/1995 | Aust et al. |
| 5,476,479 A | 12/1995 | Green et al. |
| 5,486,154 A | 1/1996 | Kelleher |
| 5,490,819 A | 2/1996 | Nicholas et al. |
| 5,498,256 A | 3/1996 | Furnish |
| 5,513,827 A | 5/1996 | Michelson |
| 5,520,678 A | 5/1996 | Heckele et al. |
| 5,522,788 A | 6/1996 | Kuzmak |
| 5,549,636 A | 8/1996 | Li |
| 5,562,699 A | 10/1996 | Heimberger et al. |
| 5,570,919 A | 11/1996 | Eusebe |
| 5,599,151 A | 2/1997 | Daum et al. |
| 5,609,601 A | 3/1997 | Kolesa et al. |
| 5,618,294 A | 4/1997 | Aust et al. |
| 5,620,415 A | 4/1997 | Lucey et al. |
| 5,624,398 A | 4/1997 | Smith et al. |
| 5,626,608 A | 5/1997 | Cuny et al. |
| 5,632,432 A | 5/1997 | Schulze et al. |
| 5,643,294 A | 7/1997 | Tovey et al. |
| 5,647,743 A | 7/1997 | Schmitt |
| 5,702,408 A | 12/1997 | Wales et al. |
| 5,704,534 A | 1/1998 | Huitema et al. |
| 5,713,505 A | 2/1998 | Huitema |
| 5,716,352 A | 2/1998 | Viola et al. |
| 5,759,151 A | 6/1998 | Sturges |
| 5,792,164 A | 8/1998 | Lakatos et al. |
| 5,807,376 A | 9/1998 | Viola et al. |
| 5,813,813 A | 9/1998 | Daum et al. |
| 5,823,066 A | 10/1998 | Huitema et al. |
| 5,827,323 A | 10/1998 | Klieman et al. |
| 5,836,960 A | 11/1998 | Kolesa et al. |
| 5,845,540 A | 12/1998 | Rosheim |
| 5,846,183 A | 12/1998 | Chilcoat |
| 5,872,808 A | 2/1999 | Davidovici et al. |
| 5,873,817 A | 2/1999 | Kokish et al. |
| 5,899,425 A | 5/1999 | Corey Jr. et al. |
| 5,899,428 A | 5/1999 | Gauger |
| 5,912,658 A | 6/1999 | Bergamasco et al. |
| 5,916,146 A | 6/1999 | Allotta et al. |
| 5,916,147 A | 6/1999 | Boury |
| 5,921,956 A | 7/1999 | Grinberg et al. |
| 5,938,678 A | 8/1999 | Zirps et al. |
| 5,947,984 A | 9/1999 | Whipple |
| 5,961,532 A | 10/1999 | Finley et al. |
| 6,019,722 A | 2/2000 | Spence et al. |
| 6,042,555 A | 3/2000 | Kramer et al. |
| 6,050,996 A | 4/2000 | Schmaltz et al. |
| 6,122,295 A | 9/2000 | Kato et al. |
| 6,161,543 A | 12/2000 | Cox et al. |
| 6,250,532 B1 | 6/2001 | Green et al. |
| 6,256,486 B1 | 7/2001 | Barany et al. |
| 6,270,453 B1 | 8/2001 | Sakai |
| 6,413,229 B1 | 7/2002 | Kramer et al. |
| 6,446,850 B2 | 9/2002 | Ming-Shun |
| 6,464,704 B2 | 10/2002 | Schmaltz et al. |
| 6,471,641 B2 | 10/2002 | Sakamoto |
| 6,471,696 B1 | 10/2002 | Berube et al. |
| 6,482,149 B1 | 11/2002 | Torii |
| 6,491,626 B1 | 12/2002 | Stone et al. |
| 6,563,856 B1 | 5/2003 | O'Shea et al. |
| 6,571,042 B1 | 5/2003 | Kordahi |
| 6,605,105 B1 | 8/2003 | Cuschieri et al. |
| 6,626,824 B2 | 9/2003 | Ruegg et al. |
| 6,635,071 B2 | 10/2003 | Boche et al. |
| 6,638,213 B2 | 10/2003 | Ogura et al. |
| 6,638,287 B2 | 10/2003 | Danitz et al. |
| RE38,335 E | 11/2003 | Aust et al. |
| 6,641,528 B2 | 11/2003 | Torii |
| 6,644,532 B2 | 11/2003 | Green et al. |
| 6,666,854 B1 | 12/2003 | Lange |
| 6,669,254 B2 | 12/2003 | Thom et al. |
| 6,676,676 B2 | 1/2004 | Danitz et al. |
| 6,682,541 B1 | 1/2004 | Gifford, III et al. |
| 6,730,020 B2 | 5/2004 | Peng et al. |
| 6,743,239 B1 | 6/2004 | Kuehn et al. |

(56) References Cited

U.S. PATENT DOCUMENTS

| | | |
|---|---|---|
| 6,746,443 B1 | 6/2004 | Morley et al. |
| 6,749,560 B1 | 6/2004 | Konstorum et al. |
| 6,752,823 B2 | 6/2004 | Prestel |
| 6,764,445 B2 | 7/2004 | Ramans et al. |
| 6,773,327 B1 | 8/2004 | Felice et al. |
| 6,817,972 B2 | 11/2004 | Snow |
| 6,824,548 B2 | 11/2004 | Smith et al. |
| 6,843,794 B2 | 1/2005 | Sixto, Jr. et al. |
| 6,858,005 B2 | 2/2005 | Ohline et al. |
| 6,902,560 B1 | 6/2005 | Morley et al. |
| 6,942,613 B2 | 9/2005 | Ewers et al. |
| 6,945,979 B2 | 9/2005 | Kortenbach et al. |
| 6,960,162 B2 | 11/2005 | Saadat et al. |
| 6,960,163 B2 | 11/2005 | Ewers et al. |
| 6,976,969 B2 | 12/2005 | Messerly |
| 6,994,700 B2 | 2/2006 | Elkins et al. |
| 7,090,637 B2 | 8/2006 | Danitz et al. |
| 7,138,976 B1 | 11/2006 | Bouzit et al. |
| 7,147,650 B2 | 12/2006 | Lee |
| 7,297,226 B2 | 11/2007 | Schulz et al. |
| 7,320,700 B2 | 1/2008 | Cooper et al. |
| 7,410,483 B2 | 8/2008 | Danitz et al. |
| 7,480,600 B2 | 1/2009 | Massie et al. |
| 7,553,275 B2 | 6/2009 | Padget et al. |
| 7,608,083 B2 | 10/2009 | Lee et al. |
| 7,615,066 B2 | 11/2009 | Danitz et al. |
| 7,637,905 B2 | 12/2009 | Saadat et al. |
| 7,678,117 B2 | 3/2010 | Hinman |
| 7,682,307 B2 | 3/2010 | Danitz et al. |
| 7,708,758 B2 | 5/2010 | Lee et al. |
| 7,785,252 B2 | 8/2010 | Danitz et al. |
| 7,828,808 B2 | 11/2010 | Hinman et al. |
| 7,842,028 B2 | 11/2010 | Lee |
| 7,854,109 B2 | 12/2010 | Zubiate et al. |
| 8,100,824 B2 | 1/2012 | Hegeman et al. |
| 8,182,417 B2 | 5/2012 | Danitz |
| 8,535,347 B2 | 9/2013 | Danitz et al. |
| 9,072,427 B2 | 7/2015 | Hegeman et al. |
| 9,085,085 B2 | 7/2015 | Danitz et al. |
| 2001/0023313 A1 | 9/2001 | Ide |
| 2002/0050944 A1 | 5/2002 | Sheynblat et al. |
| 2002/0096177 A1 | 7/2002 | Toti et al. |
| 2002/0111604 A1 | 8/2002 | Doyle et al. |
| 2002/0156497 A1 | 10/2002 | Nagase et al. |
| 2002/0161281 A1 | 10/2002 | Jaffe et al. |
| 2002/0177750 A1 | 11/2002 | Pilvisto |
| 2003/0036748 A1 | 2/2003 | Cooper et al. |
| 2003/0050649 A1 | 3/2003 | Brock et al. |
| 2003/0073939 A1 | 4/2003 | Taylor et al. |
| 2003/0078644 A1 | 4/2003 | Phan |
| 2003/0108888 A1 | 6/2003 | Scanlan et al. |
| 2003/0109898 A1 | 6/2003 | Schwarz et al. |
| 2003/0114838 A1 | 6/2003 | ONeill et al. |
| 2003/0135204 A1 | 7/2003 | Lee et al. |
| 2003/0149338 A1 | 8/2003 | Francois et al. |
| 2003/0153902 A1 | 8/2003 | Doyle et al. |
| 2003/0229271 A1 | 12/2003 | Briscoe et al. |
| 2003/0233026 A1 | 12/2003 | Saadat et al. |
| 2004/0054322 A1 | 3/2004 | Vargas |
| 2004/0138529 A1 | 7/2004 | Wiltshire et al. |
| 2004/0140786 A1 | 7/2004 | Borenstein |
| 2004/0142728 A1 | 7/2004 | Tari et al. |
| 2004/0199052 A1 | 10/2004 | Banik et al. |
| 2004/0266423 A1 | 12/2004 | Morikawa et al. |
| 2005/0070241 A1 | 3/2005 | Northcutt et al. |
| 2005/0090809 A1 | 4/2005 | Cooper et al. |
| 2005/0119527 A1 | 6/2005 | Banik et al. |
| 2005/0180351 A1 | 8/2005 | Peric |
| 2006/0009759 A1 | 1/2006 | Christian et al. |
| 2006/0020287 A1 | 1/2006 | Lee et al. |
| 2006/0036255 A1 | 2/2006 | Pond, Jr. et al. |
| 2006/0041188 A1 | 2/2006 | Dirusso et al. |
| 2006/0058582 A1 | 3/2006 | Maahs et al. |
| 2006/0111209 A1 | 5/2006 | Hinman et al. |
| 2006/0111210 A1 | 5/2006 | Hinman |
| 2006/0199999 A1 | 9/2006 | Ikeda et al. |
| 2006/0201130 A1 | 9/2006 | Danitz |
| 2007/0276430 A1 | 11/2007 | Lee et al. |
| 2007/0287993 A1 | 12/2007 | Hinman et al. |
| 2008/0065116 A1 | 3/2008 | Lee et al. |
| 2008/0188869 A1 | 8/2008 | Weitzner et al. |
| 2008/0188871 A1 | 8/2008 | Smith et al. |
| 2008/0255421 A1 | 10/2008 | Hegeman et al. |
| 2008/0255588 A1 | 10/2008 | Hinman |
| 2008/0255608 A1 | 10/2008 | Hinman et al. |
| 2008/0262538 A1 | 10/2008 | Danitz et al. |
| 2009/0067850 A1 | 3/2009 | Mizutani et al. |
| 2009/0232125 A1 | 9/2009 | Kim et al. |
| 2009/0295631 A1 | 12/2009 | Wu et al. |
| 2010/0041945 A1 | 2/2010 | Isbell, Jr. |
| 2010/0226264 A1 | 9/2010 | Axmon et al. |
| 2010/0234831 A1 | 9/2010 | Hinman et al. |
| 2010/0249759 A1 | 9/2010 | Hinman et al. |
| 2010/0261964 A1 | 10/2010 | Danitz et al. |
| 2010/0261971 A1 | 10/2010 | Danitz et al. |
| 2010/0262075 A1 | 10/2010 | Danitz et al. |
| 2010/0262161 A1 | 10/2010 | Danitz et al. |
| 2010/0305717 A1 | 12/2010 | Tong et al. |
| 2010/0316038 A1 | 12/2010 | Osato et al. |
| 2011/0022078 A1 | 1/2011 | Hinman |
| 2011/0087071 A1 | 4/2011 | Danitz et al. |
| 2011/0156957 A1 | 6/2011 | Waite et al. |
| 2012/0146834 A1 | 6/2012 | Karr |
| 2012/0300755 A1 | 11/2012 | Ancora et al. |

FOREIGN PATENT DOCUMENTS

| | | |
|---|---|---|
| EP | 0836833 A2 | 4/1998 |
| EP | 1132041 A2 | 9/2001 |
| EP | 0836833 A3 | 9/2002 |
| EP | 1395398 B1 | 1/2006 |
| EP | 1830590 | 9/2007 |
| JP | S57123101 U | 7/1982 |
| JP | H0360621 A | 3/1991 |
| JP | H06262549 A | 9/1994 |
| JP | H0723896 A | 1/1995 |
| JP | 2001299768 A2 | 10/2001 |
| WO | WO-9320878 A1 | 10/1993 |
| WO | WO-9849961 A1 | 11/1998 |
| WO | WO-0110292 A1 | 2/2000 |
| WO | 0159936 | 8/2001 |
| WO | WO-0197694 A1 | 12/2001 |
| WO | WO-0213682 A1 | 2/2002 |
| WO | WO-02087420 A2 | 11/2002 |
| WO | WO-03001986 A2 | 1/2003 |
| WO | WO-2004019769 A1 | 3/2004 |
| WO | WO-2004105578 A9 | 4/2005 |
| WO | WO-2005067785 A1 | 7/2005 |
| WO | WO-2005120326 A2 | 12/2005 |
| WO | WO-2005120327 A2 | 12/2005 |
| WO | WO-2006057699 A1 | 6/2006 |
| WO | WO-2006057700 A1 | 6/2006 |
| WO | WO-2006057702 A2 | 6/2006 |
| WO | WO-2006073581 A2 | 7/2006 |

OTHER PUBLICATIONS

Written Opinion of the International Searching Authority dated Apr. 9, 2013 for PCT Application No. PCT/FI2012/051262.
International Search Report dated Apr. 9, 2013 for PCT Application No. PCT/FI2012/051262.
Extended European Search Report dated Aug. 3, 2015. for European Application No. 12859314.2.
Cox J.L., "The Minimally Invasive Maze-III Procedure," Operative Techniques in Thoracic and Cardiovascular Surgery, W.B. Saunders Company, 2000, vol. 5 (1), pp. 79-92.
Extended European Search Report for Application No. EP14168730.1 dated Dec. 15, 2014, 6 pages.
Hegeman et al; U.S. Appl. No. 11/787,201 entitled "Articulating tool with improved tension member system", filed Apr. 16, 2007.

(56) References Cited

OTHER PUBLICATIONS http://engr.bd.psu.edu/pkoch/plasticdesign/snap_design.htm date verified via internet archive (Sep. 2, 2003).
International Search Report and Written Opinion for Application No. PCT/US2005/018146, dated Dec. 20, 2005, 12 pages.
International Search Report and Written Opinion for Application No. PCT/US2005/033377, dated May 11, 2006, 15 pages.
International Search Report and Written Opinion for Application No. PCT/US2008/060385, dated Jul. 15, 2008, 8 pages.
International Search Report and Application No. PCT/US2005/018145 (WO2005120326), dated Feb. 20, 2006, 5 pages.
International Search Report dated Aug. 26, 2005 for PCT Application No. PCT/US04/15944 filed May 21, 2004, 1 page.
International Search Report dated Jan. 25, 2006 for PCT Application No. PCT/US2005/033257 filed on Sep. 15, 2005, 2 pages.
Invitation to Pay Additional Fees dated Feb. 13, 2006 for PCT Application No. PCT/US2005/033377 filed on Sep. 19, 2005, 6 pages.
Merriam-Webster, "Define—reciprocal", Merriam-Webster's Collegiate Dictionary, 2009, p. 1038, Edition 11, Merriam-Webster, In corp, Published in: US.
Prasad S.M., et al., "Epicardial Ablation on the Beating Heart. Progress Towards on Off-Pump Maze Procedure," The Heart Surgery Forum, Forum Multimedia Publishing, LLC, 2002, vol. 5 (2), pp. 100-104.
Simha P.M., et al., "The Elctrocautery Maze—How I Do It," The Heart Surgery Forum. Forum Multimedia Publishing, LLC, 2001, vol. 4 (4), pp. 340-345.
Supplementary European Search Report for Application No. EP04752882.3, dated Feb. 6, 2013, 3 pages.
U.S. Appl. No. 10/648,911, filed Sep. 24, 2004 for Danitz et al., 57 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Written Opinion for Application No. PCT/US04/15944, dated Aug. 26, 2005, 3 pages.
Written Opinion for Application No. PCT/US2005/033257, dated Jan. 25, 2006, 7 pages.

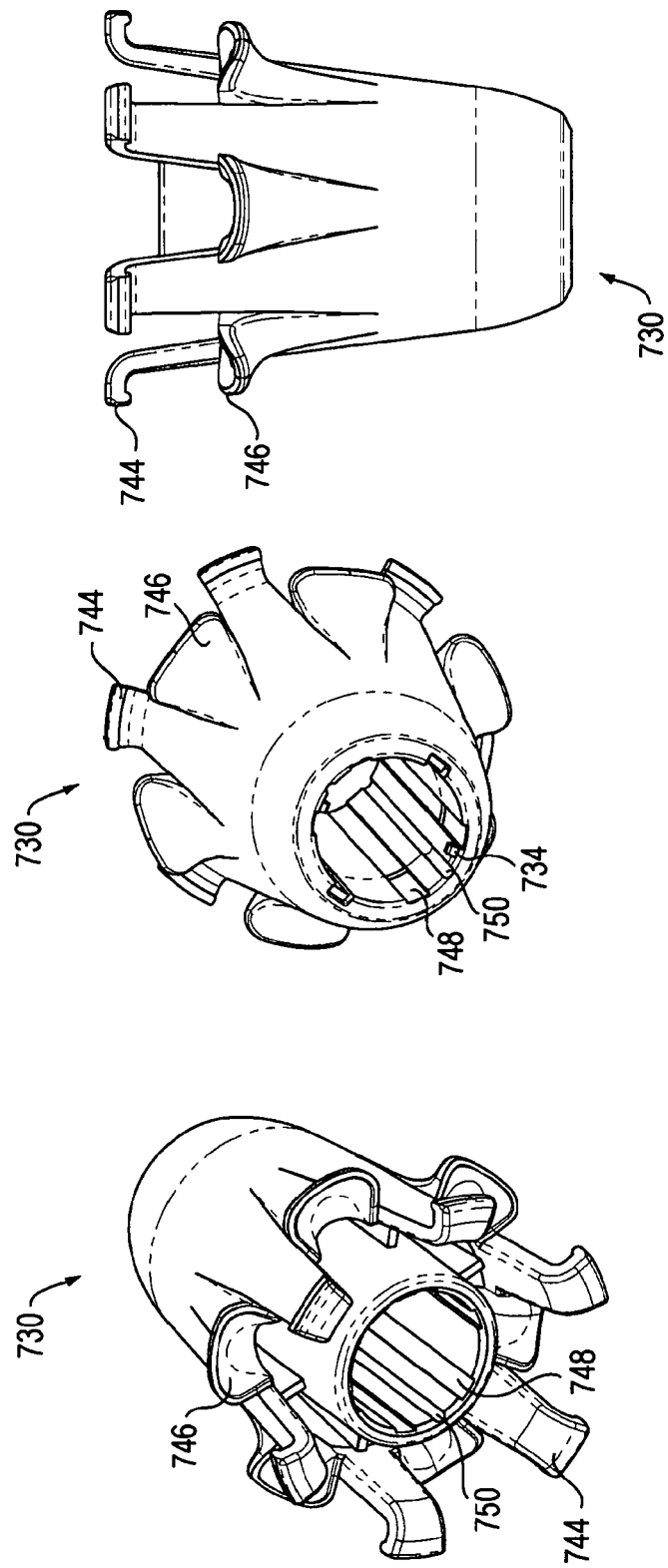

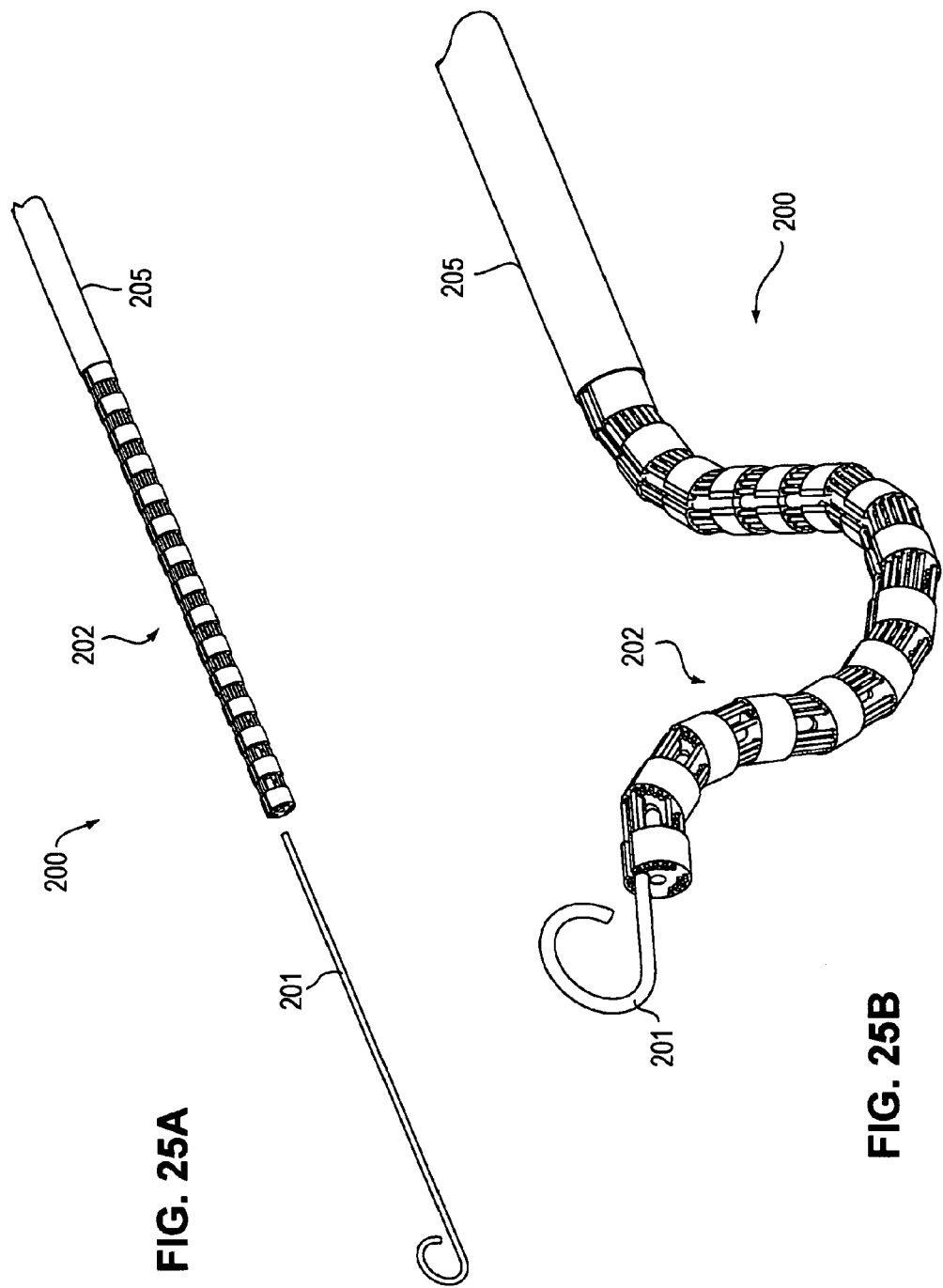

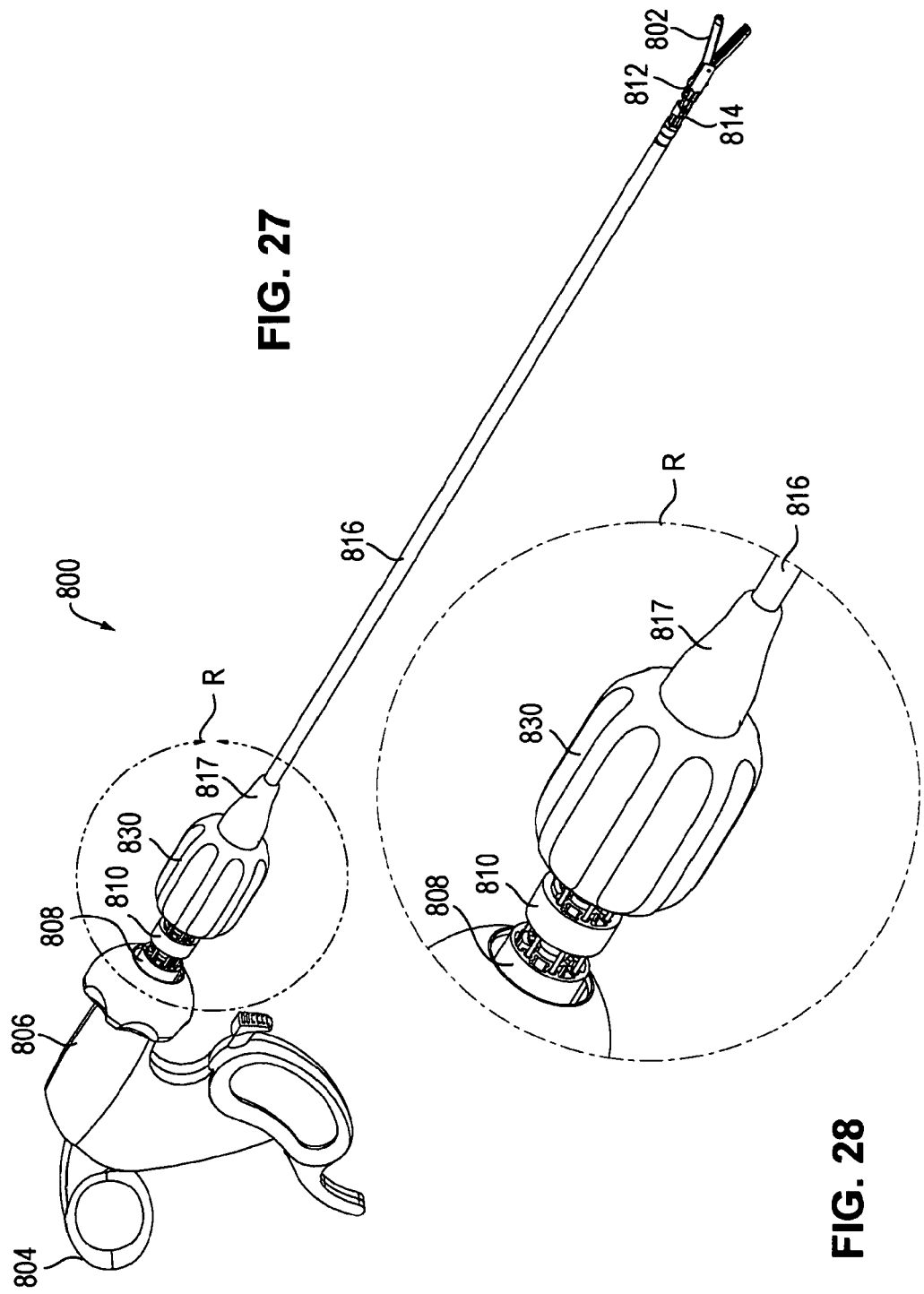

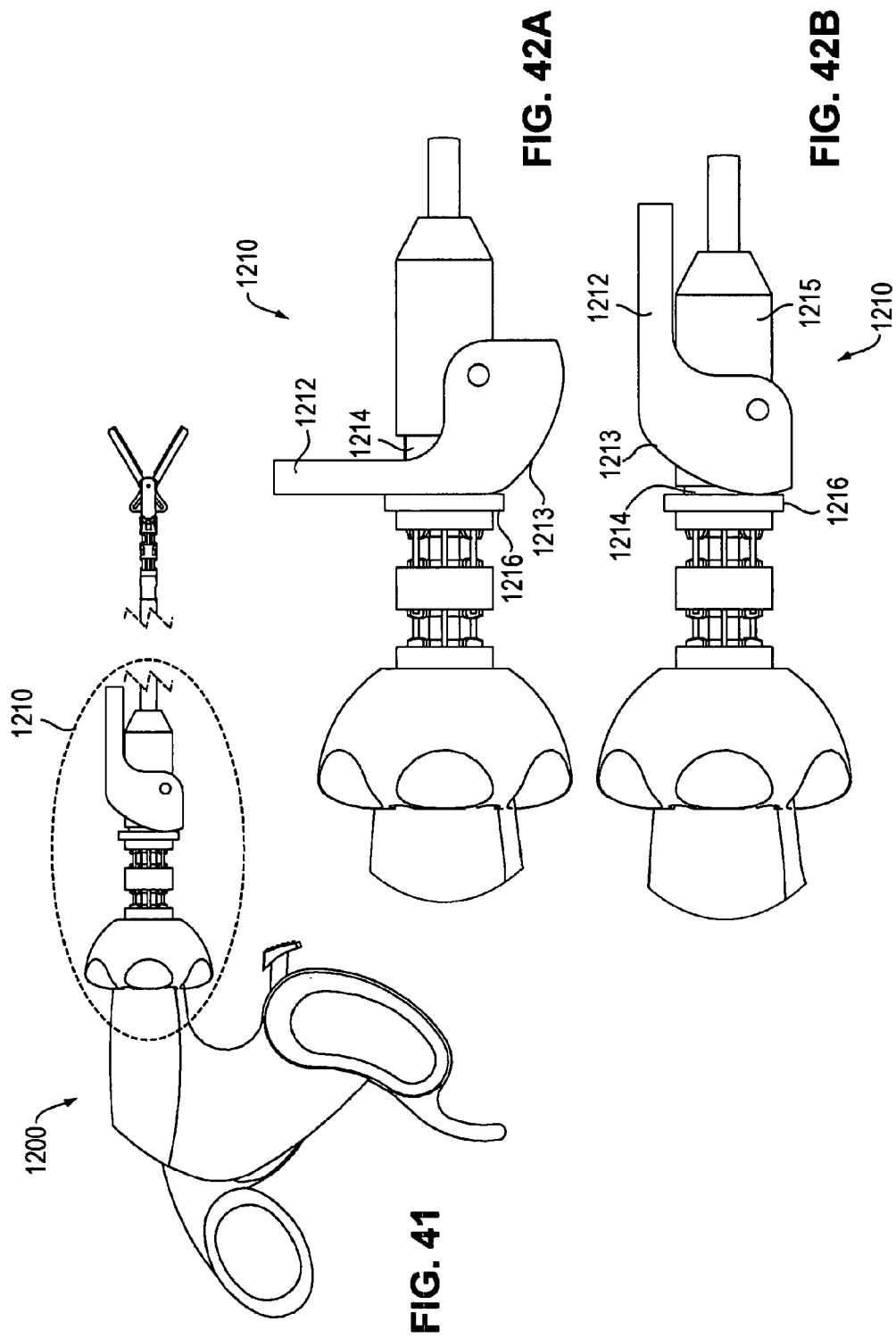

TOOL WITH ARTICULATION LOCK

CROSS REFERENCE TO RELATED APPLICATIONS

This application is a continuation of U.S. patent application Ser. No. 13/334,628 (filed Dec. 22, 2011), which is a divisional of U.S. patent application Ser. No. 11/787,543 (filed Apr. 16, 2007), now U.S. Pat. No. 8,100,824, which is a continuation in part of U.S. patent application Ser. No. 11/181,445 (filed Jul. 13, 2005), now U.S. Pat. No. 7,615,066 B2, which is a continuation of U.S. patent application Ser. No. 10/444,769 (filed May 23, 2003), now U.S. Pat. No. 7,090,637 B2, the disclosures of which are incorporated herein by reference. U.S. patent application Ser. No. 11/787,543 This application is also a continuation in part of U.S. patent application Ser. No. 11/121,668 (filed May 3, 2005), now U.S. Pat. No. 8,182,417, which claims priority to U.S. Provisional Patent Application No. 60/630,912 (filed Nov. 24, 2004), the disclosures of which are also incorporated by reference. U.S. patent application Ser. No. 11/787,543 is further related to the following concurrently filed U.S. patent applications: U.S. patent application Ser. No. 11/787,607 (filed Apr. 16, 2007; "Tool with rotation lock" of Hinman and Danitz), U.S. patent application Ser. No. 11/787,599 (filed Apr. 16, 2007, "Tool with end effector force limiter" of Hinman and Bertsch), U.S. patent application Ser. No. 11/787,605 filed Apr. 16, 2007, "Tool with multi-state ratcheted end effector" of Hinman), and U.S. patent application Ser. No. 11/787,608 (filed Apr. 16, 2007, "Articulating tool with improved tension member system" of Hegeman, Danitz, Bertsch, Alvord, and Hinman).

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

This invention relates to articulating mechanisms and applications thereof, including the remote guidance and manipulation of surgical or diagnostic tools.

BACKGROUND OF THE INVENTION

Surgical procedures such as endoscopy and laparoscopy typically employ instruments that are steered within or towards a target organ or tissue from a position outside the body. Examples of endoscopic procedures include sigmoidoscopy, colonoscopy, esophagogastro-duodenoscopy and bronchoscopy. Traditionally, the insertion tube of an endoscope is advanced by pushing it forward, and retracted by pulling it back. The tip of the tube may be directed by twisting and general up/down and left/right movements. Oftentimes, this limited range of motion makes it difficult to negotiate acute angles (e.g., in the rectosigmoid colon), creating patient discomfort and increasing the risk of trauma to surrounding tissues.

Surgical procedures such as endoscopy and laparoscopy typically employ instruments that are steered within or towards a target organ or tissue from a position outside the body. Examples of endoscopic procedures include sigmoidoscopy, colonoscopy, esophagogastroduo-denoscopy, and bronchoscopy, as well as newer procedures in natural orifice transluminal endoscopic surgery ("NOTES"). Traditionally, the insertion tube of an endoscope is advanced by pushing it forward, and retracted by pulling it back. The tip of the tube may be directed by twisting and general up/down and left/right movements. Oftentimes, this limited range of motion makes it difficult to negotiate acute angles (e.g., in the rectosigmoid colon), creating patient discomfort and increasing the risk of trauma to surrounding tissues.

Laparoscopy involves the placement of trocar ports according to anatomical landmarks. The number of ports usually varies with the intended procedure and number of instruments required to obtain satisfactory tissue mobilization and exposure of the operative field. Although there are many benefits of laparoscopic surgery, e.g., less postoperative pain, early mobilization, and decreased adhesion formation, it is often difficult to achieve optimal retraction of organs and maneuverability of conventional instruments through laparoscopic ports. In some cases, these deficiencies may lead to increased operative time or imprecise placement of components such as staples and sutures.

Steerable catheters are also well known for both diagnostic and therapeutic applications. Similar to endoscopes, such catheters include tips that can be directed in generally limited ranges of motion to navigate a patient's vasculature. There have been many attempts to design endoscopes and catheters with improved steerability. For example, U.S. Pat. No. 3,557,780 to Sato; U.S. Pat. No. 5,271,381 to Ailinger et al.; U.S. Pat. No. 5,916,146 to Alotta et al; U.S. Pat. No. 6,270,453 to Sakai, and U.S. Pat. No. 7,147,650 to Lee describe endoscopic instruments with one or more flexible portions that may be bent by actuation of a single set of wires. The wires are actuated from the proximal end of the instrument by rotating pinions (Sato), manipulating knobs (Ailinger et al.), a steerable arm (Alotta et al.), by a pulley mechanism (Sato), or by manipulation of complementary portions (Lee). U.S. Pat. No. 5,916,147 to Boury et al. discloses a steerable catheter having four wires that run within the catheter wall. Each wire terminates at a different part of the catheter. The proximal ends of the wires extend loosely from the catheter so that the physician may pull them. The physician is able to shape and thereby steer the catheter by selectively placing the wires under tension.

Recently, surgical instruments, including minimally invasive surgical instruments, have been developed that are more ergonomic and which have a wider range of motion and more precise control of movement. These instruments may include mechanisms that articulate using a series of links coupled with one or more sets of tension bearing members, such as cables. As with conventional instruments used in minimally invasive surgery, rotation of the shaft and the end effector with respect to the handle is an important feature of cable and link type instruments to aid with dissecting, suturing, retracting, knot tying, etc. Ergonomic, flexible, and intuitive mechanisms that facilitate manual control and placement of the end effectors of such instruments are also important factors as medical procedures become more advanced, and as surgeons become more sophisticated in operating abilities. Further improvements in the features and design of surgical instruments are desirable.

SUMMARY OF THE INVENTION

It may at times be desirable to maintain the orientation or configuration of the distal end of steerable or articulating instruments that have use in medical fields or non-medical applications. This invention provides methods and devices for locking or otherwise maintaining the shape and orientation of steerable and articulating instruments.

Embodiments of the invention include a tool that includes a distal portion and a proximal portion, an articulation mechanism, and an articulation lock. In some embodiments of the tool, the tool is for medical applications, such as is a surgical or diagnostic tool. The articulation mechanism manipulates the angular orientation or configuration of the distal portion; it includes a pair of links, each pair including a proximal link and a distal link spaced apart from each other. The mechanism is adapted such that movement of the proximal link causes corresponding relative movement of the distal link. The relative movement of the distal link that corresponds to the proximal link movement may either mirror the movement of the proximal link or be reciprocal to it.

The articulation lock has an engaged state and a disengaged state, wherein in the engaged state the articulation lock impedes movement of the proximal link and corresponding relative movement of the distal link. In some embodiments the impeding of movement is a partial impeding of movement; in other embodiments the impeding is a substantial blocking or preventing of movement. In some embodiments impeding the movement of the proximal link causes the impeding of the corresponding relative movement of the distal link.

In some embodiments the tool further includes an end effector disposed at the distal portion. In some embodiments the end effector includes a surgical or diagnostic mechanism. In some embodiments the tool includes an end effector actuator disposed at the proximal portion. In some embodiments the tool includes a handle at a proximal end of the tool, and the handle includes the end effector actuator.

Some embodiments have an articulation lock that includes a link friction increasing element, such that when the lock is engaged, increased friction impedes movement of the links. Increasing friction can partially impede link movement such that the link movement is malleable. Increasing friction can also fully impede link movement such that link movement is substantially blocked or prevented. Thus at the baseline level of friction that manifests on the link surfaces, the links can be considered freely moveable. With increasing levels of friction, link movement is such that the articulation mechanism as a whole is malleable, and with further increase in friction, the articulation mechanism seizes such that there is substantially no movement. With the articulation mechanism in an articulated configuration, application of friction can prevent movement of links from that articulated configuration.

Some embodiments of the articulation mechanism include tension load bearing members connecting the links of link pairs; some of these embodiments include an articulation lock that includes a tension member adjusting mechanism to increase tension on the members. Some embodiments of tension load bearing members include cables, and such members may frequently be referred to simply as cables. Increasing tension on the cables increases friction on link surfaces that impedes link movement. As summarized above, increasing friction with a cable tension adjusting mechanism can impede movement of links such that they can move malleably or links may be substantially unable to move.

In some embodiments, the articulation lock includes a rigid element, which when the lock is engaged, is disposed such that it extends at least from a point proximal to the proximal link to a point at least distal to the proximal link. In other embodiments, the articulation lock includes a malleable element, which when the lock is engaged, is disposed such that it extends at least from a point proximal to the proximal link to a point at least distal to the proximal link. The articulation lock embodiments that include a malleable locking element are able lock the links in an articulated configuration.

In addition to an articulation mechanism and an articulation lock, some embodiments further include an end effector disposed at the distal portion; the end effector may comprise a surgical or diagnostic mechanism. The tool may further include a handle at the proximal end of the tool, and the handle may comprise an end effector actuator.

In embodiments of the tool, the relative movement of the distal link that corresponds to the movement of the proximal link in some embodiments may be reciprocal to the movement of the proximal link; in other embodiments the movement of the distal link may mirror the movement of the proximal link.

In some embodiments the articulation mechanism includes multiple pairs of corresponding links, a proximal link on the proximal portion of the tool and a distal link on the distal portion of the tool, such that movement of the proximal link causes corresponding relative movement of the distal link. Thus in typical embodiments, the proximal link of a pair that is most proximal on a tool operably corresponds to the distal link that is most distal on the tool. Similarly, the most distal proximal link corresponds to the most proximal distal link. Accordingly, intermediate proximal links accordingly correspond to intermediate distal links.

In addition to an articulation mechanism and an articulation lock, some embodiments further include an end effector disposed at the distal portion; an end effector actuator disposed at the proximal portion; a shaft disposed between the end effector and the end effector actuator; such that movement of the distal link causes angular movement of the end effector with respect to the shaft. In some of these embodiments, the articulation mechanism includes multiple pairs of links, each pair including a proximal link on the proximal portion of the tool and a distal link on the distal portion of the tool, such that movement of the proximal link causes corresponding relative movement of the distal link and angular movement of the end effector with respect to the shaft.

In some of the tool embodiments with an end effector, an end effector actuator, a shaft, and multiple pairs of links, the articulation mechanism includes tension load bearing members connecting the links and the articulation lock includes a tension load bearing member tension adjusting mechanism configured to increase tension on the members. In some embodiments the tension load bearing members comprise cables, accordingly, such tension load bearing members may be referred to as cables; accordingly, the tension load bearing member adjusting mechanism may be commonly referred to as a cable tension adjusting mechanism In some embodiments, the cable tension adjusting mechanism is disposed between the proximal and the distal links; in other embodiments the cable tension adjusting mechanism is disposed proximal to the most proximal link. In some of these embodiments, the cable tension adjusting mechanism includes a threaded member; in other embodiments, the cable tension adjusting mechanism includes a cam locking lever configured to increase the length of the shaft, thereby increasing tension on the cables. The cable tension adjusting mechanism, whether tensioned by a threaded member or a cam lever or any other mechanism, acts to vary the distance between the proximal and distal links. By such varying of distance, friction that resists movement between links can vary. These just-summarized embodiments of an articulation lock can lock links in an articulated configuration as well as in an unarticulated configuration.

In some of the tool embodiments with an end effector, an end effector actuator, a shaft, and multiple pairs of links, the articulation lock includes a locking rod disposed in a channel formed in one or more links. In some embodiments, the locking rod is rigid; in some it is malleable. When the locking rod is malleable, the articulation lock can lock links in an articulated configuration.

In some of these embodiments with an end effector, an end effector actuator, a shaft, and multiple pairs of links, the articulation lock includes a locking sleeve fitted over the multiple proximal links. In some embodiments, the locking sleeve is rigid; in some it is malleable. When the locking sleeve is malleable, the articulation lock can lock links in an articulated configuration.

In some of these just summarized tool embodiments with an end effector, an end effector actuator, a shaft, and multiple pairs of links, the articulation lock includes a rigid element which, when engaged, is disposed at least from a point proximal to the most proximal proximal link to at least to a point distal to the most distal proximal link. In some of these embodiments, the rigid element is disposed adjacent to the proximal links when in the engaged state. In some of these embodiments, the rigid element includes a sleeve that at least partially surrounds the proximal links when in the engaged state. In some of these embodiments, the sleeve is slidably mounted on the tool. In some of these embodiments with a slidable sleeve, the sleeve is disposed distal to the proximal links when in the disengaged state.

Embodiments of the invention include methods for using a tool, the tool comprising a distal portion and a proximal portion, an articulation mechanism and an articulation lock, the method including changing the position of the lock. In some embodiments, the tool is a medical tool configured for surgical or diagnostic methods. The articulation mechanism is for manipulating angular orientation of the distal portion, the articulation mechanism comprising at least one pair of links, the pair comprising a proximal link on the proximal portion and a distal link on the distal portion, the mechanism adapted such that movement of the proximal link causes corresponding relative movement of the distal link and the distal portion of the tool. The articulation lock has a disengaged state wherein the links move freely, and an engaged state wherein the lock impedes movement of the proximal link and corresponding relative movement of the distal link.

The tool may further include an end effector disposed at the distal portion of the tool, such that movement of the distal portion of the tool moves the end effector. The tool may further include an end effector actuator disposed at the proximal portion of the tool, such that moving the end effector actuator causes moving of the proximal link. In some embodiments, the tool may include a handle at the proximal end of the tool, and the handle may comprise the end effector actuator. In addition to an end effector disposed at the distal portion and an end effector actuator disposed at the proximal portion, the tool may further include a shaft disposed between the end effector and the end effector actuator; wherein movement of the distal link causes angular movement of the end effector with respect to the shaft.

The method of changing the position of the lock may be applied to a lock in a disengaged state, and wherein the changing the position comprises engaging the lock. Engaging the lock may be applied to a tool wherein the articulation mechanism comprises tension load bearing members (cables for example), connecting the links and the articulation lock comprises a tension load bearing member (cable) tension adjusting mechanism configured to increase cable tension when engaging the lock. Engaging a lock with a cable tension adjusting mechanism may be applied to an articulation mechanism when it is in either an unarticulated configuration (which can be understood as a neutral or straight configuration), or it can be applied to an articulation mechanism when it is in an articulated configuration, in which case the articulated configuration is maintained as the mechanism is locked. Engaging a lock with a cable tension adjusting mechanism may include increasing tension on cables such that movement of the articulation mechanism is partially impeded; and by having its movement partially impeded, the articulation mechanism becomes malleable. Engaging a lock with a cable tension adjusting mechanism may also include increasing tension on the cables such that movement of the articulation mechanism is substantially blocked. Exemplary embodiments of a lock including a cable tension adjusting mechanism include a threaded element for increasing tension on the cables, and a cam lever mechanism for adjusting the length of the shaft, lengthening the shaft having the effect of increasing tension on the cables.

The changing of position such that the lock becomes engaged may be applied to a tool with a lock that includes a rigid element, and wherein engaging the lock comprises placing the rigid element where it extends from a point proximal to the proximal link to a point distal to the proximal link, and wherein engaging the lock substantially blocks movement of the distal portion. In some embodiments, the rigid element is a rod, in some embodiments the rigid element is a sleeve.

Engaging the lock may be applied to a tool with a lock that includes a malleable element, and wherein engaging the lock comprises placing the lock in a position where it extends from a point proximal to the proximal link to a point distal to the proximal link. Engaging a lock with a malleable element may be applied to an articulation mechanism when it is in either a neutral or unarticulated configuration, or it can be applied to an articulation mechanism when it is in an articulated configuration, in which case the articulated configuration is maintained. Exemplary embodiments of a malleable element include a rod and a sleeve.

The method of changing the position of the lock may be applied to a lock in an engaged state, and wherein the changing the position comprises disengaging the lock. Disengaging the lock may be applied to a tool wherein the lock comprises a cable tension adjusting mechanism configured to decrease cable tension when disengaging the lock. The cable tension adjusting mechanism may include a threaded member for decreasing tension in the cables. The cable tension adjusting mechanism may include a cam lever for adjusting the length of the shaft.

Disengaging the lock may be applied to a tool wherein the lock comprises a rigid element, and wherein the rigid element is removed from a position where it extends from a point proximal to the proximal link to a point distal to the proximal link.

Disengaging the lock may be applied to a tool wherein the lock comprises a malleable element, and wherein the malleable element is removed from a position where it extends from a point proximal to the proximal link to a point distal to the proximal link.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings which are briefly described below.

FIGS. 9-13 show the sleeve support mechanism in the unlocked position. FIG. 9 is a cross-sectional focus on details of a pair of shoulders formed in the sleeve, a corresponding pair of shoulder stops, a pair of detents on the sleeve that correspond to a pair of detents on the sleeve support.

FIG. 10 is a full cross sectional side view of the sleeve and sleeve support mechanism, with a circled portion representing the location of detail shown in FIG. 9.

FIG. 11 is a surface side view of the sleeve and sleeve support mechanism corresponding to the cross-sectional view of FIG. 10.

FIG. 12 is a proximal-looking perspective view of the sleeve encircled around the sleeve support, the sleeve in an unlocked position.

FIG. 13 is a distal-looking perspective view of the sleeve encircled around the sleeve support, the sleeve in an unlocked position.

FIG. 14 is a proximal-looking perspective view of sleeve encircled around the sleeve support, the sleeve m a locked position.

FIG. 20 is a distal-looking perspective view of the sleeve without the sleeve support.

FIG. 21 is a proximal-looking perspective view of the sleeve without the sleeve support.

FIG. 22 is a side view of the sleeve without the support mechanism, proximal end up.

FIG. 25A and FIG. 25B provide views of an articulation lock comprising a rod: FIG. 25A shows a rod, which as depicted could either be a rigid rod or a malleable rod, oriented for insertion into the proximal portion of a multi-link articulating mechanism. FIG. 25B shows a malleable rod in place within the mechanism, holding the mechanism in an articulated configuration.

FIG. 26A proximal-looking perspective view; FIG. 26B is a distal looking perspective view.

FIG. 27 is a member of a series extending through FIG. 34 showing another embodiment of the tool. FIG. 27 is a perspective view showing an embodiment that is configured with a cylindrical sleeve comprising an internal threaded portion (not shown in this surface view), and with ball and socket type links. This articulation lock embodiment is of a type that adjusts the tension bearing members that connect articulating links, thereby increasing friction between links Encircled section of FIG. 27 is shown in greater detail in FIG. 28.

FIG. 28 is an enlarged detail of FIG. 27, focusing on the cylindrical sleeve, and showing proximal links and a shaft extension portion.

FIG. 31 shows the shaft extension portion, on the proximal portion of the shaft, from a proximal-looking perspective, with threads on the proximal portion.

FIG. 32 shows the shaft extension portion, on the proximal portion of the shaft, from a distal-looking perspective, with threads on the proximal portion, and showing holes and lumens for cables to pass through.

FIG. 34 shows the threaded plug portion of the articulation lock from a proximal-looking perspective, showing the lumens to permit cable sets to pass through.

FIG. 41 is a side view of an instrument with cam-based articulation locking mechanism that is located between proximal and distal links. The cam mechanism effectively increases the length of the shaft. This articulation lock embodiment is of a type that adjusts tension on the tension bearing members that connect articulating links, thereby increasing friction between links. The lever shown in an unlocked position, thereby allowing articulation.

FIGS. 42A and 42B provide detail views of the cam lock of FIG. 41. FIG. 42A depicts a locked position, and FIG. 42B depicts an unlocked position. The detail view emphasizes the difference in relative location of the telescoping shaft components in the two positions.

FIG. 43A shows the lock in the unlocked position; FIG. 43B shows the lock in the locked position. This embodiment has no dedicated end effector; the mechanism itself serves as the engaging portion of the tool.

FIG. 45A shows an articulated configuration and FIG. 45B shows a straight, unarticulated position.

DETAILED DESCRIPTION OF THE INVENTION

Articulating Instruments

Figure 1:
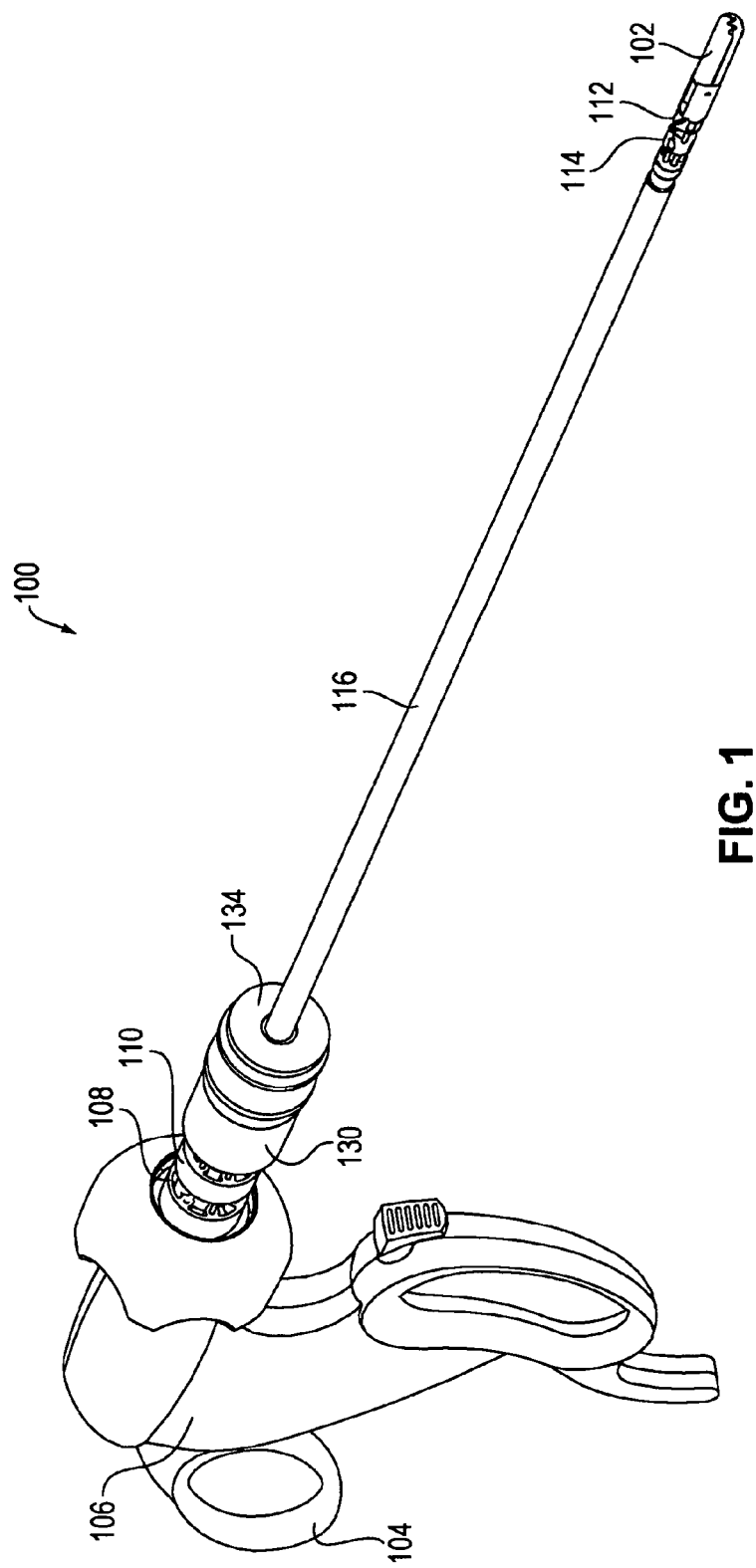
FIG. 1 is a front perspective view of an articulatable surgical tool.

Steerable articulating instruments are described in U.S. Pat. No. 7,090,637; US 2005/0107667; US 2005/0273084; US 2005/0273085; US 2006/0111209, and US 2006/0111210. The articulating mechanisms of the tools described in those publications use multiple pairs of segments or links controlled, e.g., by multiple sets of cables, as well as tools that have a single pair of links, connected by a single set of cables, such as those described in U.S. Pat. No. 5,916,146. Depending upon the specific design of the device, the links can be discrete segments (as described, e.g., in U.S. Pat. No. 7,090,637) or discrete portions of a flexible segment (as described, e.g., in US 2005/0173085). The instrument may also include steerable or controllable links, e.g., as described in US 2005/0273084, US 2006/0111209, and US 2006/0111210. Embodiments of the invention are not specific to any particular type of link, and may include any type of link known in the art.

When using such articulating instruments, a user may manipulate the proximal end of the instrument, thereby moving one or more proximal links of the articulation mechanism. This movement results in relative movement of the distal link(s) corresponding to the proximal link(s). It may at times be desirable to lock or otherwise maintain the straight or bent shape of the instrument. In certain embodiments of this invention, the shape of the instrument is maintained by preventing movement of at least one of the proximal links with respect to the rest of the instrument.

FIGS. 1-6 show an articulatable tool 100 with an end effector 102 at its distal end and an end effector actuator 104 within a handle 106 at its proximal end. Instrument 100 may be used, e.g., in a laparoscopic procedure requiring grasping or cutting within a patient. Exemplary embodiments of the tool 100 may also may useful in endoscopic procedures, particularly when, as in some embodiments, the tool has a flexible shaft. Still other embodiments may be used for percutaneous procedures, such as a catheter. Still other embodiments include devices that are directed toward natural orifice transluminal endoscopic surgery ("NOTES"). Embodiments of the invention may include a wide variety of tools, some with medical or diagnostic purposes, and others that are applied to other types of tasks where the articulational capabilities of the tool provide benefit. Proximal articulation links 108 and 110 extend distally from handle 106, and distal articulation links 112 and 114 extend proximally from end effector 102. Proximal link 108 is connected to and moves with handle 106. Likewise, distal link 112 is connected to and moves with end effector 102. An elongated shaft 116 is disposed between the proximal links and the distal links.

Figure 2:
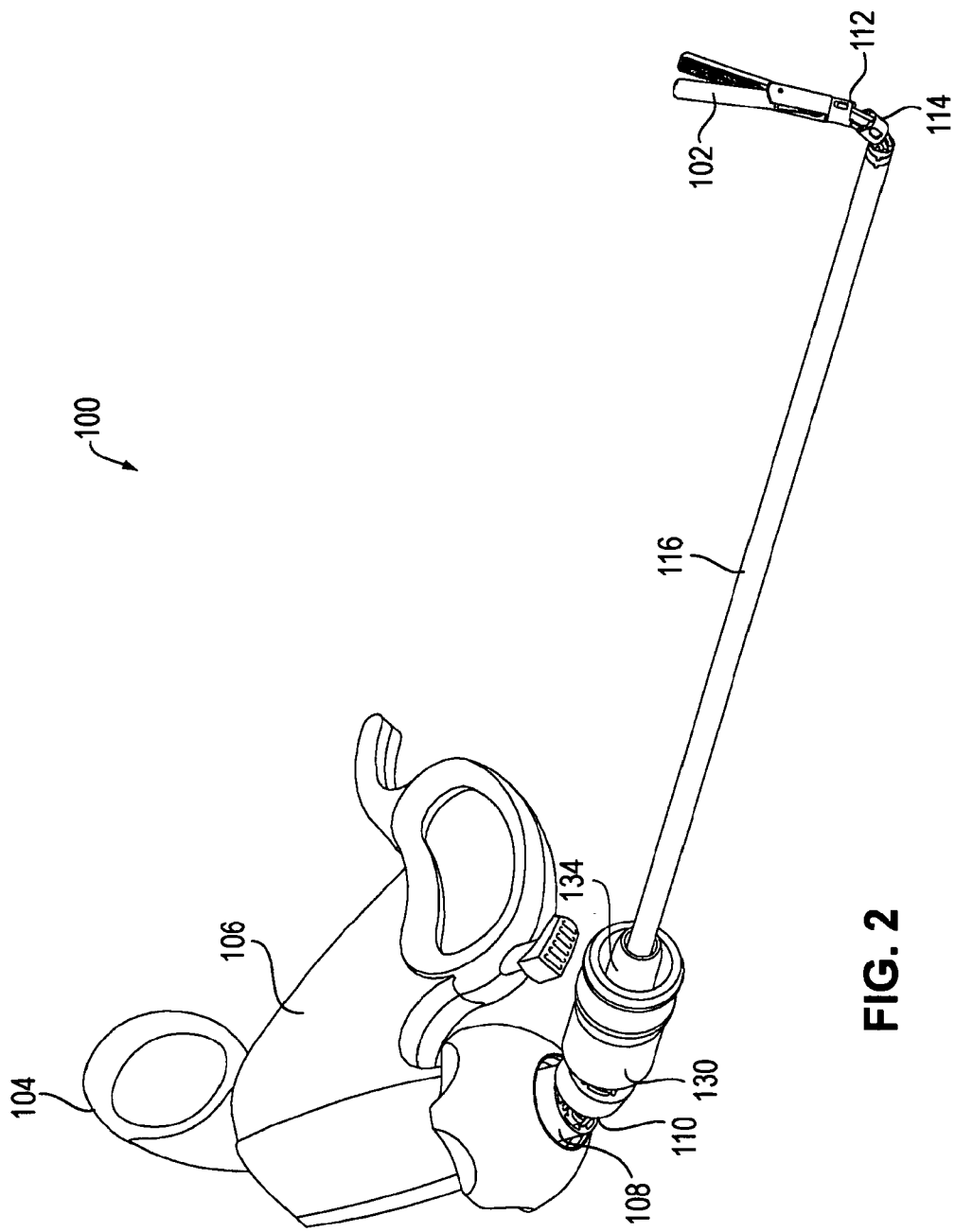
FIG. 2 is perspective view of a surgical tool in an articulated position.

Proximal and distal links of paired links are operably connected by tension bearing members, such as cables. Embodiments may include tension bearing members other than cables, but for simplicity and because cables are a typical embodiment, tension bearing members may be commonly referred to as cables. A set of control cables 118 is attached to proximal link 108, extends through proximal link 110, shaft 116 and distal link 114 and is attached to distal link 112. A second set of control cables 120 is attached to proximal link 110, extends through shaft 116 and is attached to distal link 114. In this embodiment, there are three control cables 118 in the first set and three control cables 120 in the second set. It should be appreciated, however, that other numbers of control cables may be used to connect corresponding proximal and distal links. In addition, mechanisms other than cables may be used to connect corresponding links As shown in FIG. 2, movement of handle 106 and proximal link 108 with respect to proximal link 110 moves end effector 102 and distal link 112 in a relative and corresponding manner. Likewise, movement of proximal link 110 with respect to shaft 116 moves distal link 114 with respect to shaft 116 in a relative and corresponding manner, also as shown in FIG. 2. This relative articulation movement provides a way for a user to remotely manipulate the end effector through movement of the handle.

Figure 3:
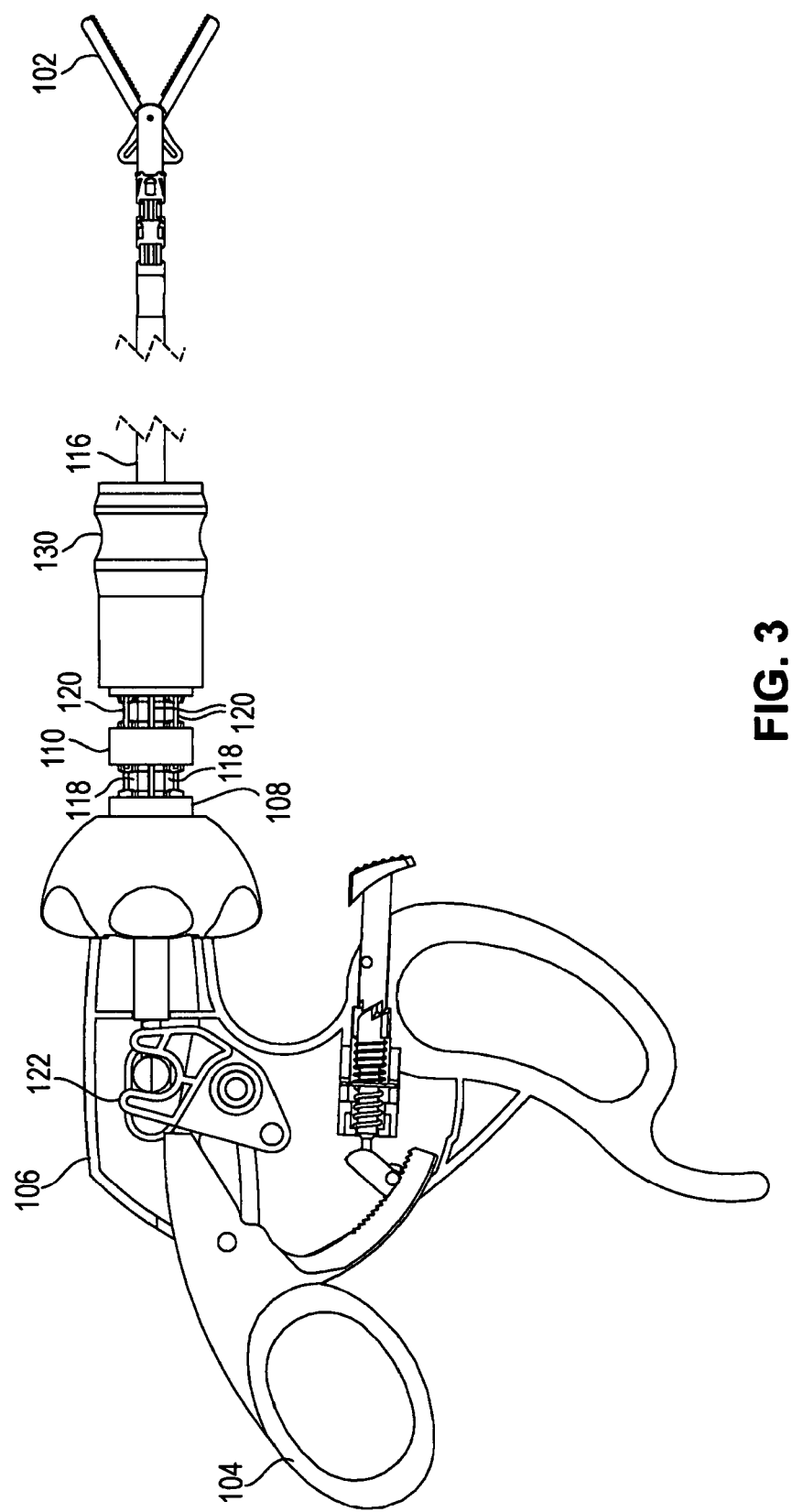
FIG. 3 is an exposed side view of a surgical tool with an end effector actuator and an end effector both in an open position.
Figure 4:
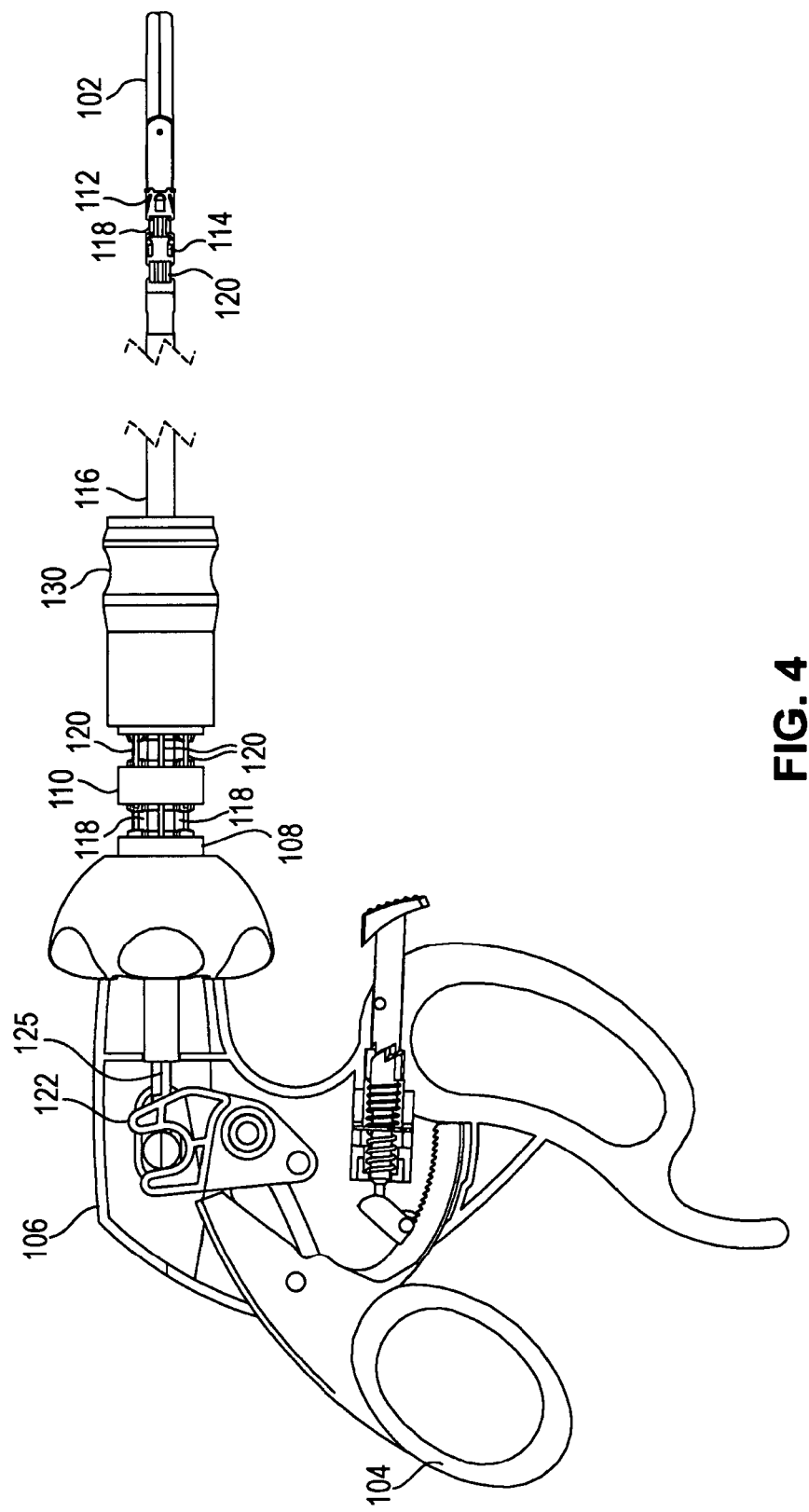
FIG. 4 is an exposed side view of a surgical tool with an end effector actuator and an end effector both in a closed position.
Figure 5:
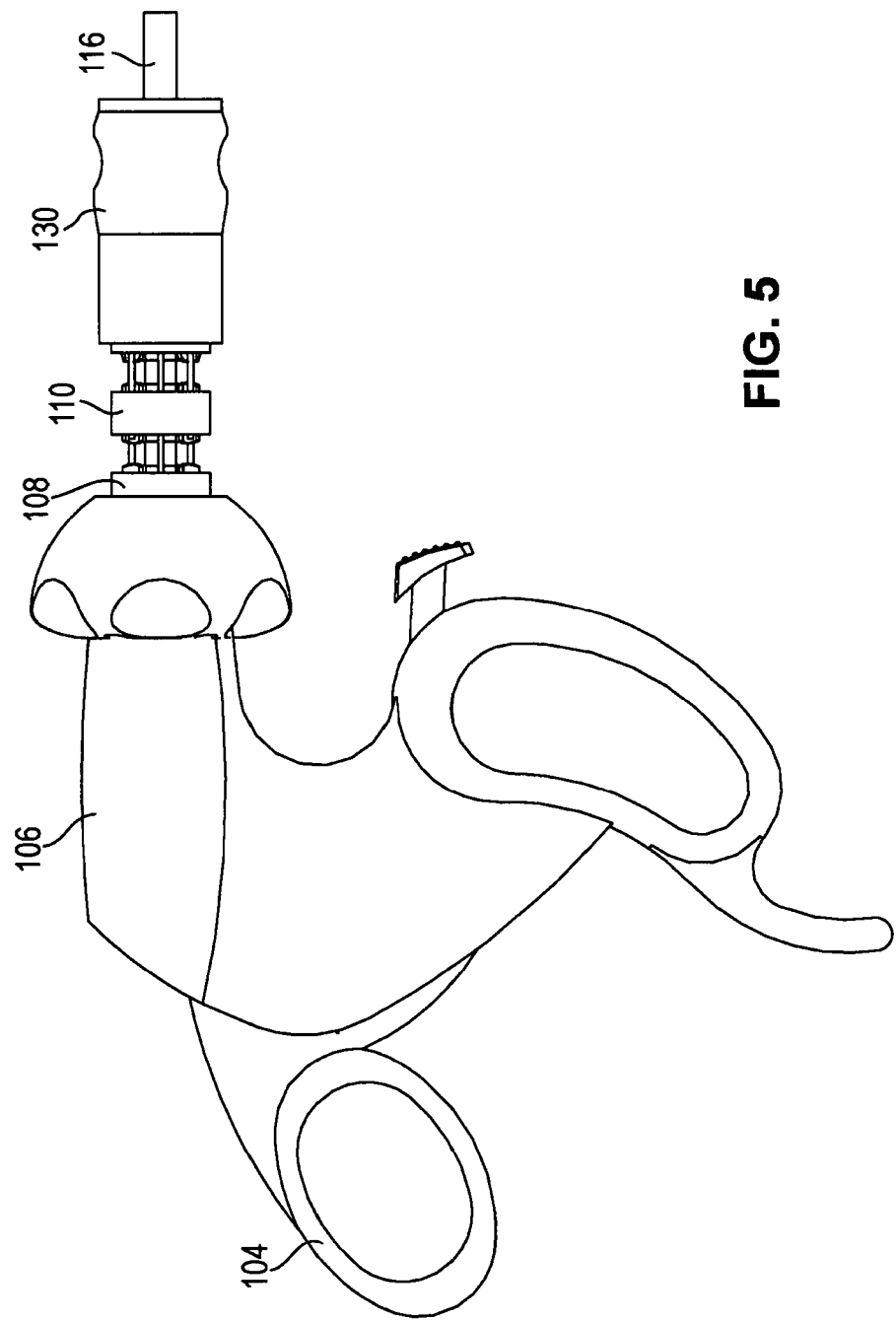
FIG. 5 is a side view of the proximal portion of a tool, showing the handle and proximal end of the shaft, with an articulation locking sleeve in a distal and unlocked position.

In the embodiment illustrated in FIGS. 1-4, the end effector 102 is a pair of jaws. Actuation force is transmitted from end effector actuator 104 through a transmission that includes a linearly movable compression bearing member or rod 125 and a rotatable rod actuator 122, as shown in FIGS. 3 and 4. In some embodiments, the tension bearing member or rod is also capable of bearing a compressive load, such that an end effector can be pushed by a force transmitted by the end effector actuator.

Other end effectors (surgical, diagnostic, etc.) and end effector actuators may be used with the articulating tool of this invention. In some embodiments, the distal links, themselves, can comprise an end effector, such as, for example, a retractor. In some embodiments, the movable tension bearing member or rod may comprise any flexible tension bearing material; in some embodiments Nitinol offers particular advantages as it is sufficiently flexible to accommodate articulation, and yet resilient enough to carry a compressive load that allows the rod to open an end effector, such as a set of jaws.

Locking Articulation by Locking Proximal Links

In order to maintain a particular position of the end effector with respect to the shaft, the articulating tool of this invention has an articulation lock. In the embodiment shown in FIGS. 1-6, the articulation lock includes a movable sleeve 130. In some embodiments the sleeve is rigid, as is the depicted example, but in other embodiments the sleeve may be malleable. Malleability may be imparted by variations in design, such as with folds in the sleeve, or by increasing of dimensions, or by use of malleable materials, or by use of combinations of materials that individually contribute flexibility or stiffness, or by any combination of these approaches. In the unlocked position shown in FIGS. 1-5, sleeve 130 is distal to proximal links 108 and 110. In the locked position shown in FIG. 6, however, sleeve 130 has been moved proximally to a position adjacent to and covering links 108 and 110 as well as the proximal end of shaft 116, thereby blocking relative movement between links 108 and 110 and between link 110 and shaft 116. In this locked position, relative movement between distal links 112 and 114 and between link 114 and shaft 116 is prevented as well.

Figure 6:
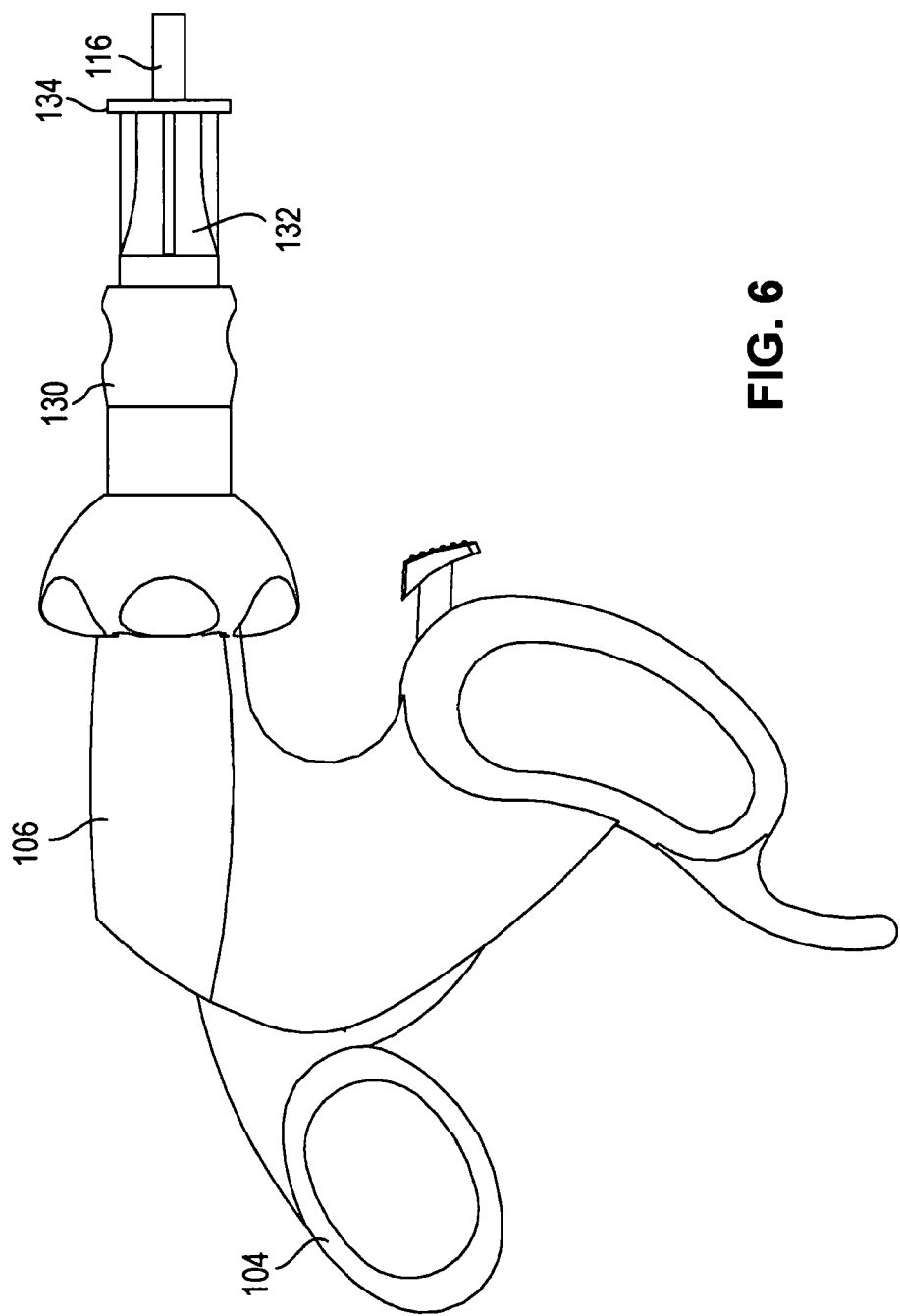
FIG. 6 is a side view of the proximal portion of a tool, showing the handle and proximal end of the shaft, with an articulation locking sleeve in a proximal and locked position.
Figure 7:
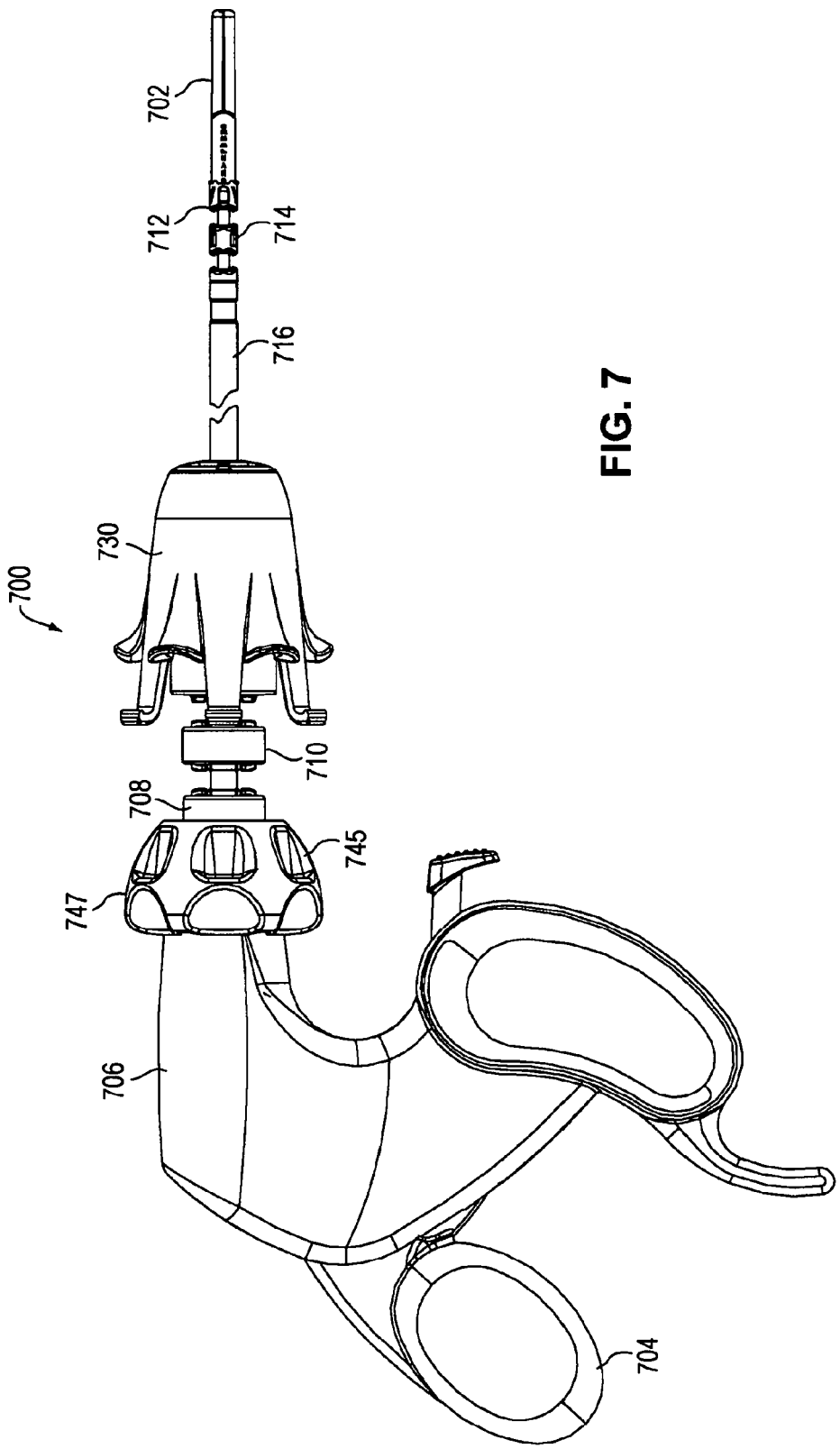
FIG. 7 is a side view of another embodiment of surgical tool, with a different embodiment of an articulation locking sleeve in distal and unlocked position, and with an end effector actuator and an end effector both in a closed position.
Figure 8:
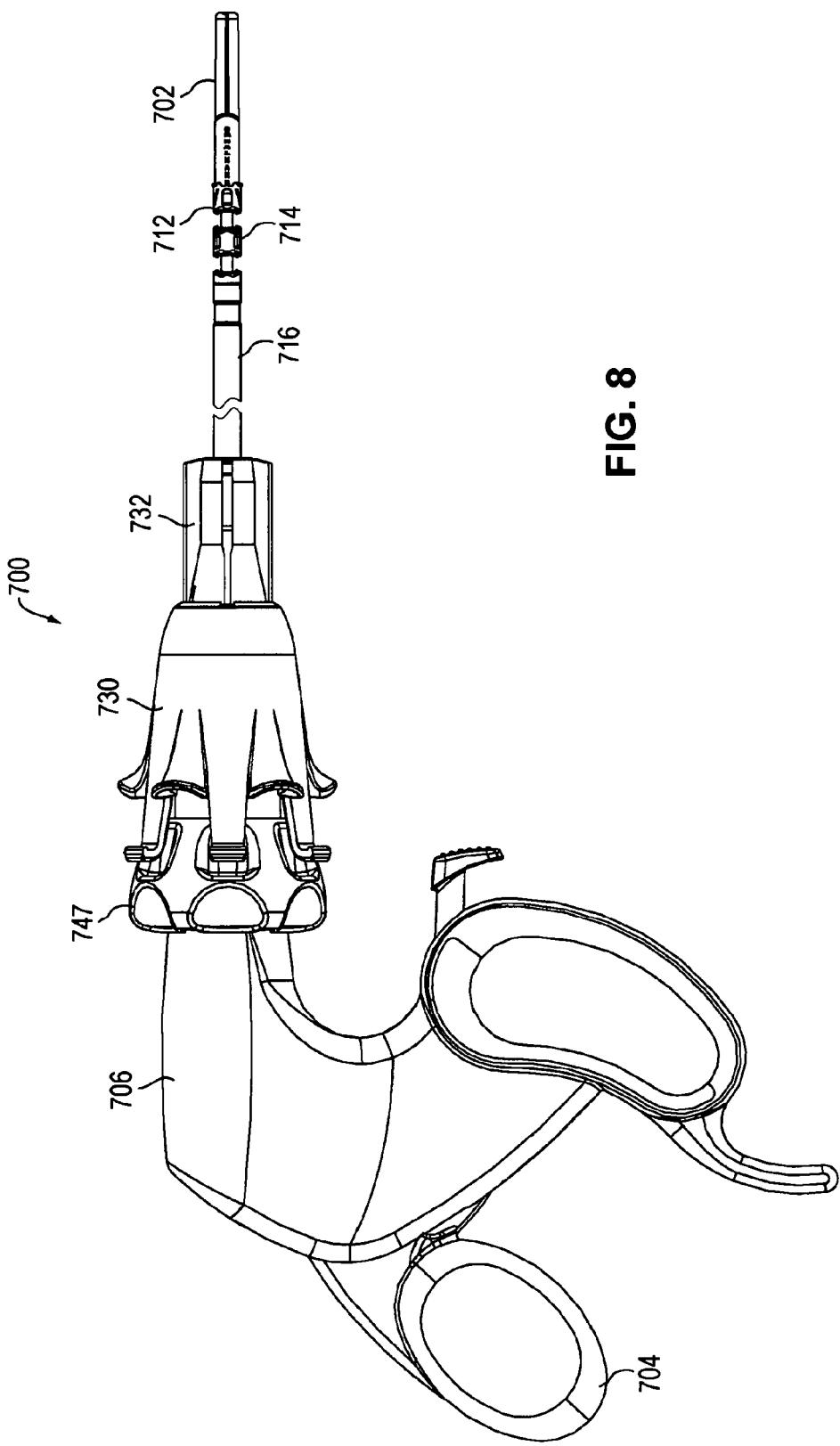
FIG. 8 is a side view of the embodiment shown in FIG. 7, but with the articulation locking sleeve in a proximal and locked position.
Figure 9:
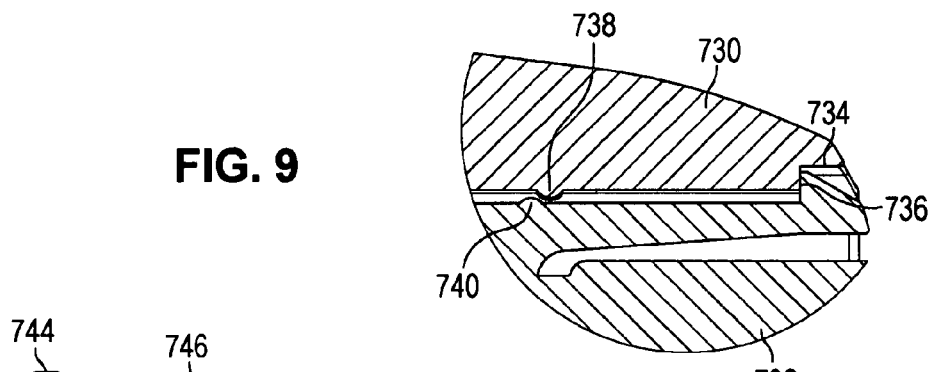
FIG. 9 is a member of a series that extends through FIG. 24, showing details of a locking sleeve support mechanism, over which the sleeve slides.
Figure 10:
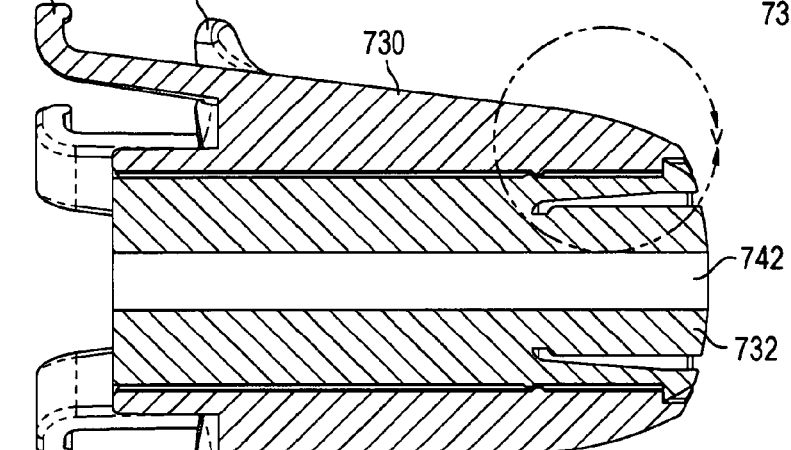
Figure 11:
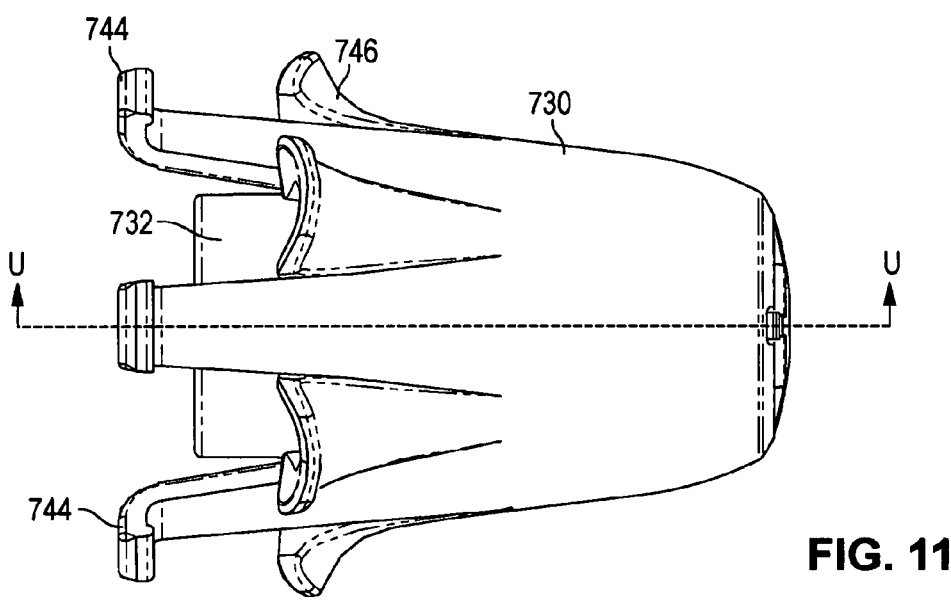
Figure 13:
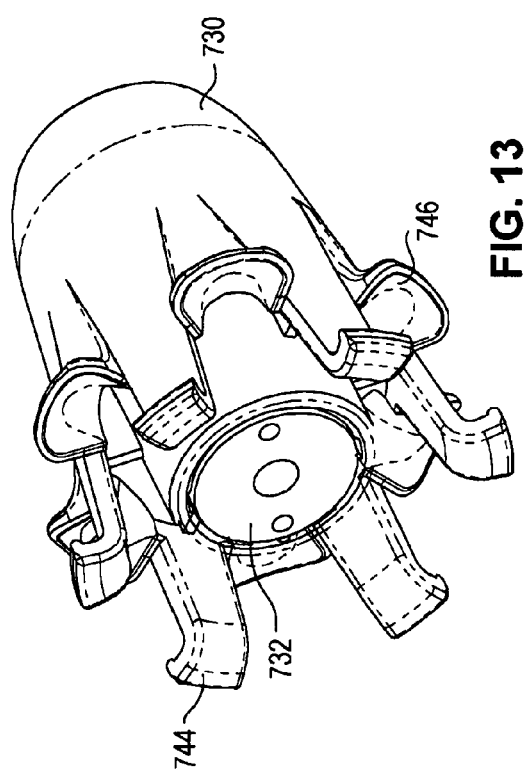
Figure 15:
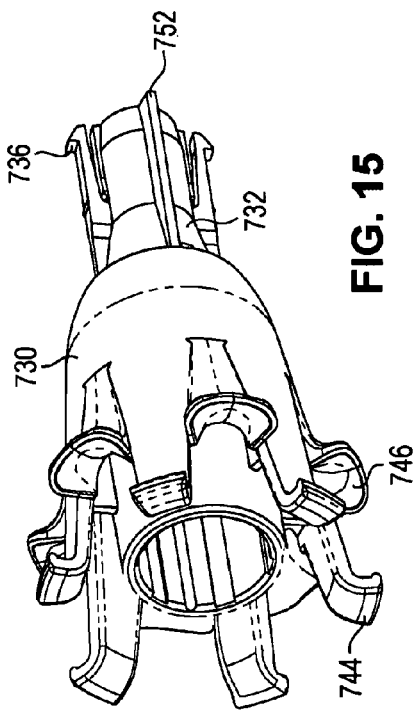
FIG. 15 is a distal-looking perspective view of sleeve encircled around the sleeve support, the sleeve in a locked position.
Figure 12:
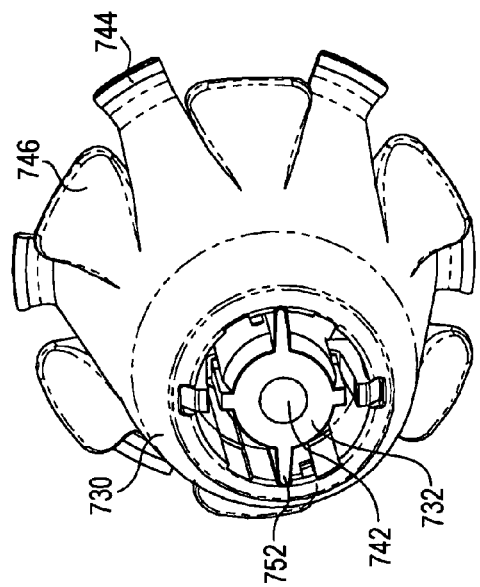
Figure 14:
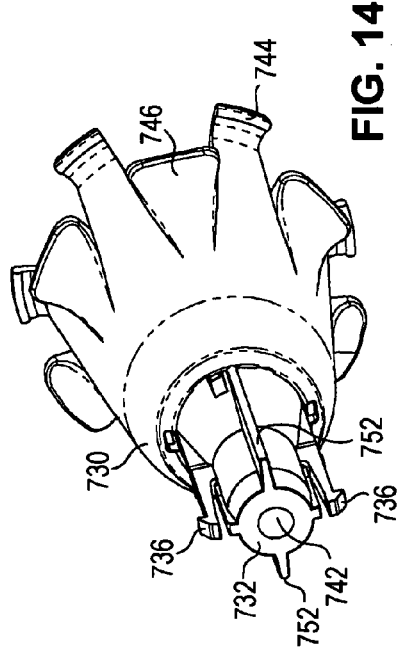
FIG. 14 is a member of a series that extends through FIG. 19 showing the sleeve and sleeve support mechanism in the locked position.
Figure 17:
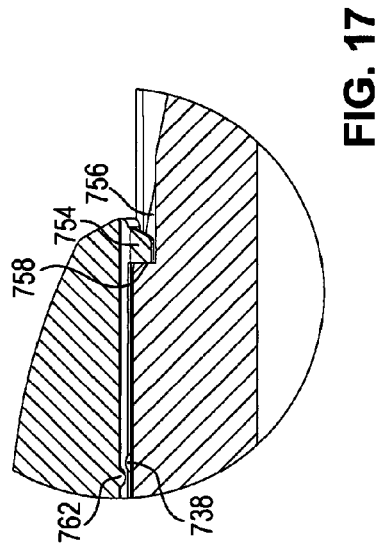
FIG. 17 is a cross-sectional focus on details of a pair of shoulders formed in the sleeve, a corresponding pair of shoulder stops, a pair of detents on the sleeve that correspond to a pair of detents on the sleeve support, the detail analogous to the view shown in FIG. 9, except that the sleeve is in a locked position.
Figure 19:
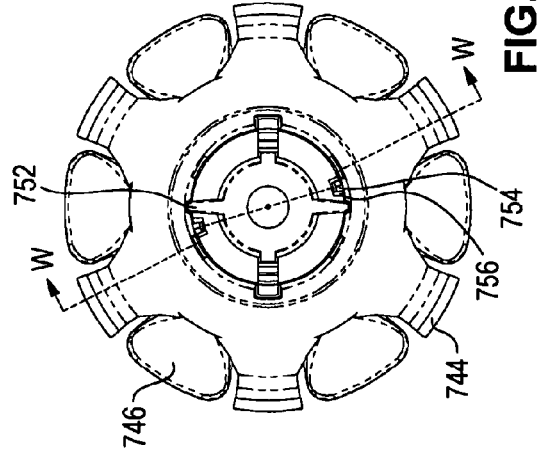
FIG. 19 is a proximal-looking front end view of the sleeve and sleeve support showing push tabs and pull tabs on the sleeve, and anti-rotation ribs on the sleeve support.
Figure 16:
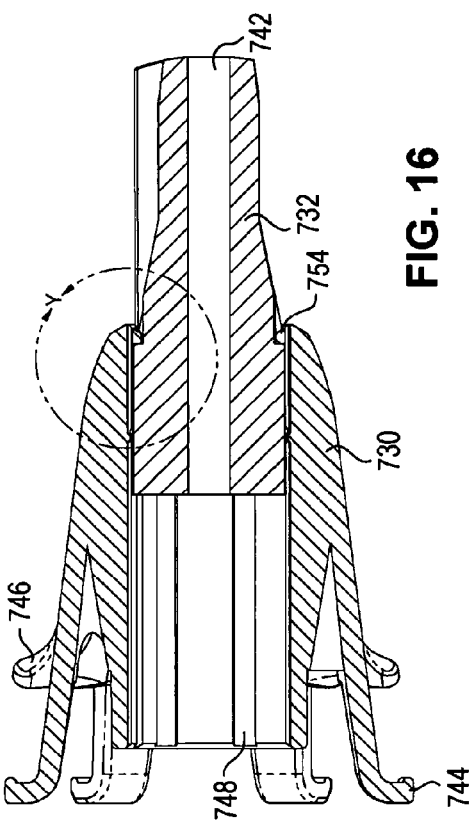
FIG. 16 is a cross-sectional side view of the sleeve and sleeve support, analogous to the view of FIG. 10, but with the sleeve in a locked position. The encircled area indicates the location of detail shown in FIG. 17.
Figure 18:
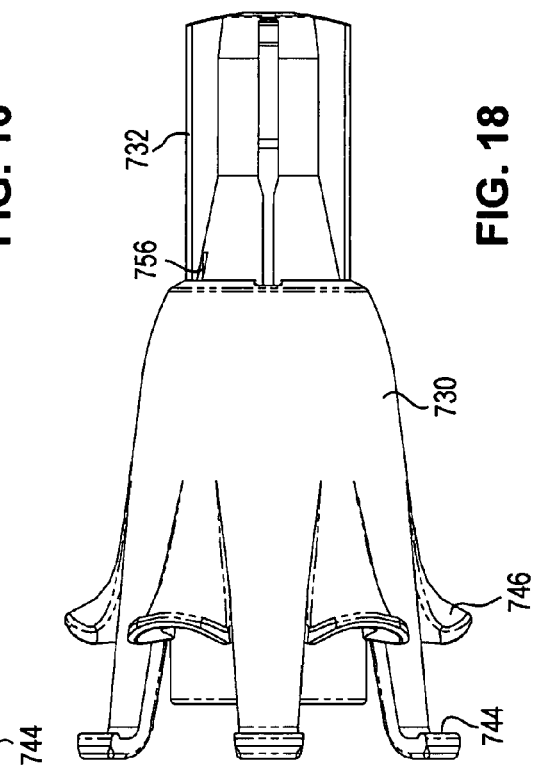
FIG. 18 is a surface side view of the sleeve and sleeve support corresponding to the cross-sectional view of FIG. 16, the sleeve in a locked position.

As shown in FIG. 6, a sleeve support mechanism 132 extends proximally from shaft 116 to provide sliding support for sleeve 130. A distal stop 134 provides a limit of distal movement of sleeve 130; a similar stop (not shown) is provided on or within handle 106 to limit proximal movement of sleeve 130. Detents, ridges or other mechanisms may be provided to maintain the sleeve in its proximal or distal positions and to provide tactile feedback to the user regarding the position of the sleeve.

FIGS. 7-24 show another embodiment of the invention. Articulatable tool 700 has an end effector 702 at its distal end and an end effector actuator 704 within a handle 706 at its proximal end. Tool 700 may be used, e.g., in a laparoscopic procedure requiring grasping or cutting within a patient. Proximal articulation links 708 and 710 extend distally from handle 706, and distal articulation links 712 and 714 extend proximally from end effector 702. Proximal link 708 is connected to and moves with handle 706. Likewise, distal link 712 is connected to and moves with end effector 702. An elongated shaft 716 is disposed between the proximal links and the distal links. The linkage between pairs of proximal and distal links may be with cables as in the embodiment of FIG. 1 or by any other suitable tension bearing members. Likewise, operation of end effector 702 may be as in the FIG. 1 embodiment. Alternative embodiments of the tool could have as few as a single pair of links, and a single cable set, or multiple pairs of links, and multiple cable sets. In any combination, the articulation lock now described would be appropriate and applicable As in the embodiment of FIGS. 1-6, movement of handle 706 and proximal link 708 with respect to proximal link 710 moves end effector 702 and distal link 712 in a relative and corresponding manner. Likewise, movement of proximal link 710 with respect to shaft 716 moves distal link 714 with respect to shaft link 716 in a relative and corresponding manner. Such movements of the distal link, in alternative embodiments, can either reciprocate or mirror the movement of the proximal link, depending on whether the cables are strung directly (for reciprocal movement), or whether they are rotated 180° (for mirrored movement). This relative articulation movement provides a way for a user to remotely manipulate the end effector through movement of the handle.

In order to maintain a particular position of the end effector with respect to the shaft, the articulating tool of this embodiment has an articulation lock. In some embodiments of the inventive locking mechanism, as described further below in the "friction locking embodiments" section, the locking mechanism provides a state that lies between free articulation and substantially blocked articulation such that movement can be characterized as being "impeded". Embodiments of mechanisms or methods described herein thus may also be characterized as mechanisms or methods that relate to permissibility of articulation such that articulation may occur freely, may occur not at all, or may occur in an impeded condition.

In the embodiment shown in FIGS. 7-24, the articulation lock includes a movable rigid sleeve 730. In the unlocked position shown in FIG. 7, sleeve 730 is distal to proximal links 708 and 710. In the locked position shown in FIG. 8, however, sleeve 730 has been moved proximally to a position adjacent to and covering links 708 and 710 as well as the proximal end of shaft 716, thereby blocking relative movement between links 708 and 710 and between link 710 and shaft 716. In this locked position, relative movement between distal links 712 and 714 and between link 714 and shaft 716, and relative movement of the end effector, are all prevented as well.

FIGS. 9-24 show details of a sleeve support mechanism 732 attached to and extending proximally from shaft 716 and its interaction with sleeve 730. In FIGS. 9-13, sleeve 730 is in the unlocked position. In this position, a pair of shoulders 734 that are formed in sleeve 730 abut a corresponding pair of shoulder stops 736 formed on support mechanism 732. In addition, a pair of detents 738 formed on sleeve 730 is just distal to a corresponding pair of detents 740 formed on sleeve support mechanism 732, as shown best in the detail view of FIG. 9. A central bore 742 provides space for the cables and the rod 125, as seen for example in FIG. 4. The links are proximal to the sleeve support mechanism. The proximal face of the sleeve support part really has ball and socket features in it (not shown). Caroming surfaces 735 on shoulder stops 736 and circumferential space 737 are provided for tool assembly purposes. As sleeve 730 is drawn proximally over sleeve support mechanism 732 during assembly, engagement of a proximal sleeve surface with caroming surfaces 735 to push shoulder stops radially inward into space 737 to permit sleeve 730 to be drawn over the support mechanism.

Sleeve has pull tabs 744 to provide a grip for a user to move the sleeve proximally. Push tabs 746 provide a similar function for moving the sleeve distally. In the locked position shown in FIG. 7, pull tabs 744 nest with grooves 745 formed in a rotation knob 747 that may, in some embodiments, be used to rotate end effector 702 with respect to handle 706 and to lock the rotational position of the end effector. Further details of such a rotation knob and lock may be found in concurrently filed US patent application "Tool rotation lock" of Hinman and Danitz, This nesting feature is optional with respect to the articulation lock of this invention.

When pulled proximally, clearance channels 748 on the inner surface of sleeve 730 permit the sleeve to slide proximally with respect to detents 740. In addition, anti-rotation channels 750 in sleeve 730 cooperate with anti-rotation ribs 752 in support mechanism 732 to prevent sleeve 730 from rotating as it moves proximally and distally.

Figure 23:
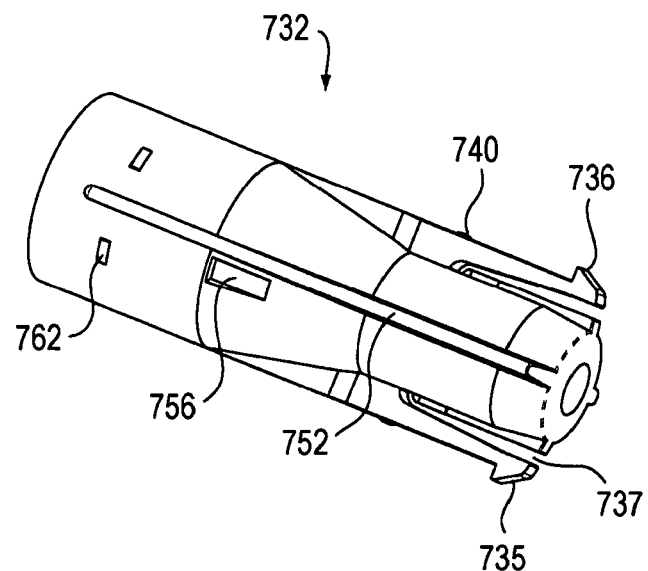
FIG. 23 is a perspective view of the isolated sleeve support mechanism.
Figure 24:
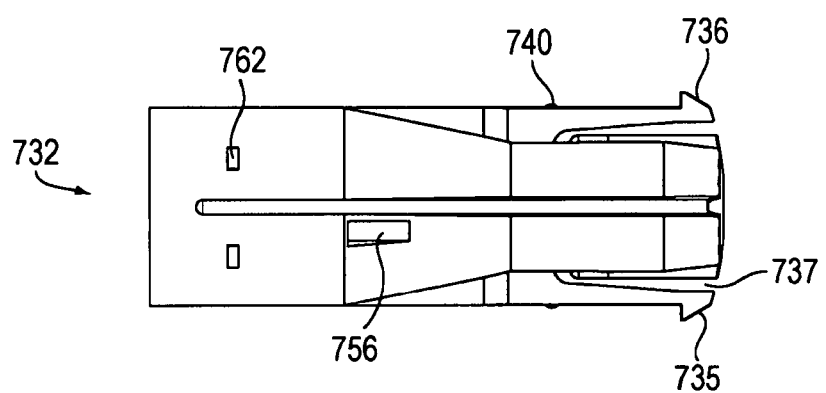
FIG. 24 is a side view of the isolated sleeve support mechanism.

FIGS. 14-19 show details of the sleeve and sleeve support mechanism of this embodiment in the locked position. As sleeve 730 is drawn proximally to provide the articulation lock, a pair of tabs 754 on sleeve 730 pass through recesses 756 in support mechanism 732 to engage stop shoulders 758. In addition, as tabs 754 draw toward shoulders 758, detents 738 on sleeve 730 pass over detents 762 on support mechanism 732 to hold sleeve 730 in the locked position and to provide further tactile feedback about the state of the articulation lock. FIGS. 20-22 show further views of sleeve 730, and FIGS. 23-24 show further views of sleeve support mechanism 732.

Typically, rigid elements lock an articulation mechanism in a single configuration, generally "straight". Some embodiments of rigid elements may not be "straight" however; as some embodiments may assume a bent or curved configuration that is desirable for a particular application. Thus, as useful as it may be for many applications, rigid element locking, in contrast to malleable locking, is a locking that is typically limited to a single locked configuration. Malleable locking mechanisms, in contrast, provide an ability that rigid elements generally lack, which is to lock an articulating mechanism in any of the various articulated configurations that the mechanism can assume.

As will be described further below, other features come with articulating mechanisms that have a locking mechanism based on friction locking, in contrast to the rigid or malleable element locking. This friction-based type of locking allows various locked states that include a substantially blocked movement (like that of rigid element lock embodiments), as well as a partially-impeded movement (similar but not identical to that of malleable element lock embodiments). The motion impedance provided by the friction lock is adjustable or tunable in degree in accordance with the degree to which tension in the mechanism is adjusted. The friction lock embodiments and features are described further in a section below.

Figure 26B:
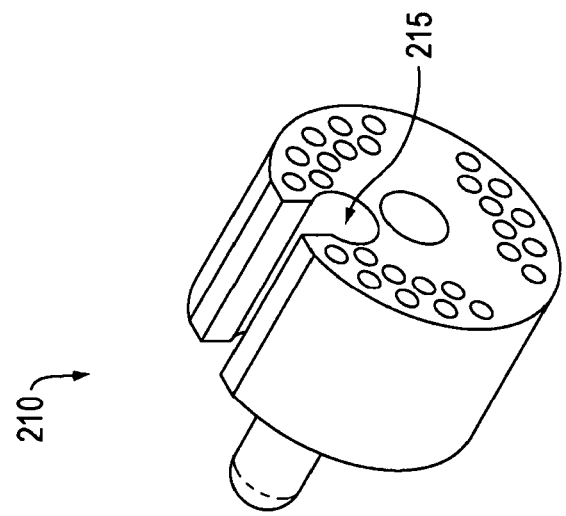
FIG. 26A and FIG. 26B provide detail views of the links depicted in FIGS. 25A and 25B.
Figure 26A:
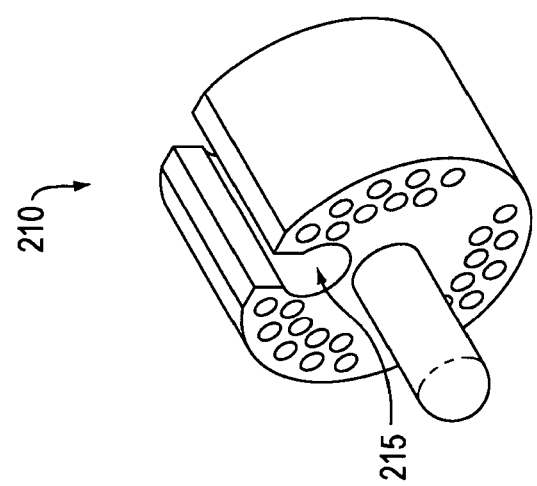

FIGS. 25 and 26 show a locking rod embodiment of an articulation lock. FIG. 25A shows a simple rod 201 aligned to be inserted into an articulating tool 200 with a set 202 of multiple links (15, in this case). Only the proximal portion of the tool is seen, it has no proximal handle, but has a shaft 205. FIG. 25A could represent either a rigid rod or a malleable rod, depending on the nature of the material from which the rod is fabricated. FIG. 25B shows the rod as a malleable rod 201, after insertion into tool 200, and after the articulating mechanism has been manipulated so as to articulate it. In the present state, the mechanism is locked. FIG. 25B also provides a perspective view of the proximal face of the most proximal link 210, where it can be seen that the rod has entered and occupies a channel 215 in the link, such channel being continuous throughout the links in the mechanism. FIGS. 26A and 26B show such a link, from a distal-looking and proximal-looking perspective, respectively. The rod channel 215 is in the form of an open groove; in other embodiments, the channel could be circumferentially closed.

It can be seen that the locking rod, whether rigid or malleable, operates by being disposed proximal to each proximal link whose movement it blocks to a point distal to each blocked proximal link. Inasmuch as the illustrated tool embodiment 200 includes 15 links, the rod is disposed proximal to the most proximal link, and extends to a point distal to the distal-most proximal locked link. In some embodiments, a proximal subset of the proximal links may be locked by a rod, leaving the more distal of the proximal links unlocked. The rod does not extend into the distal region of the articulating mechanism; it exerts its locking force only by way of locking the proximal links. The proximal links that are locked by a rod transfer the blockage of their movement to the distal links by way of the tension bearing members connecting them.

Figure 45B:
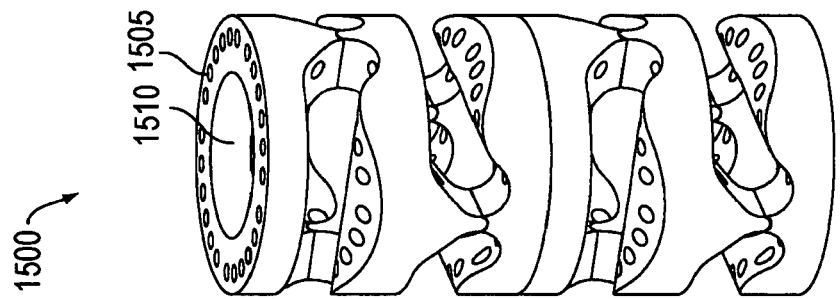
FIGS. 45A and 45B show a set of pivoting links that have a single degree of freedom.
Figure 45A:
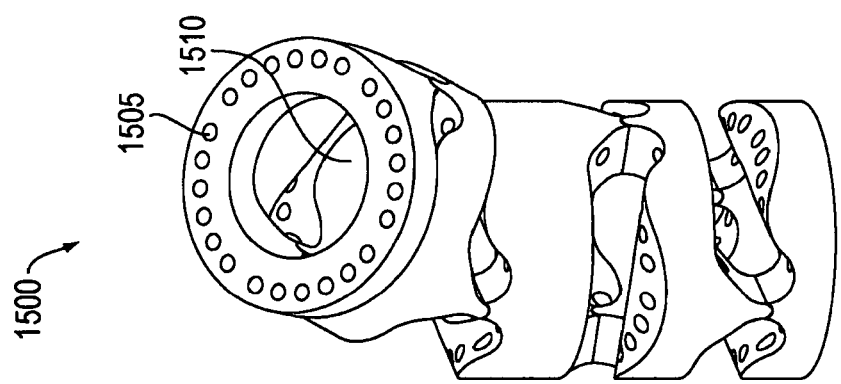

Friction Locking Embodiments: Locking by Adjusting Tension of Tension Bearing Members Articulation lock embodiments in this section arc generally of a type that involves locking movement between articulating links with friction. Links, as described above, typically occur in proximal-distal pairs that are operably connected to each other by a set of tension bearing members, such as cables. The cables are configured in such a way that movement of the proximal link transfers to the corresponding or complementary distal link of the pair by way of the cables or other tension bearing members. Some embodiments of articulating mechanism to which friction-based locking may be applied include ball and socket links, but other types of links, such as single-degree-of-freedom pivoting links, are also included as embodiments (FIGS. 45 and 46).

Friction-based locking mechanisms described herein include a mechanism that adjusts the tension of the tension bearing members. Tension can be increased either by decreasing the length of cables connecting the links while the distance between links remains unchanged, or by increasing the length of the distance between links, while not changing the length of the connecting cables. Each approach is exemplified by embodiments below.

In a neutral or unlocked position, the tension of cables is at a baseline level according to specifications appropriate for the mechanism and its application. With increasing tension, as applied by a tension adjusting mechanism, pressure between the links increases, which increases friction between the links, and the friction impedes movement across the interface between the links. Thus, by such locking mechanisms, an articulating mechanism can move from (1) an unlocked state, where links are freely movable, or movable at some baseline level of freedom, to a state (2) where movement between links is partially impeded and wherein the articulation mechanism as a whole is malleable, to a state (3) where movement between links is substantially blocked, and the articulation mechanism as a whole is "seized".

The friction locking mechanisms have other features that distinguish them from rigid- or malleable-element-based mechanisms described above. One feature characteristic of friction locking, per described embodiments, involves a locking process that occurs with substantial uniformity throughout the proximal-to-distal length of the locked portion of the articulating mechanism. (This locking process as a whole differs from the rigid or malleable element-based approaches where the direct locking action of the mechanism occurs in the one or more proximal links, and wherein the tension bearing members transfer that locked state to the distal links, causing them to lock in this secondary manner.) The locked portion of an articulating mechanism need not include the entire length. An inner portion of the length (i.e., a set of link pairs including the more distal of the proximal links and the more proximal of the distal links) may be locked, leaving the outer portion of the length (i.e., a set of link pairs including the more proximal of the proximal links and the more distal of the distal links) free to articulate. For example (referring to FIG. 4) tension could be increased in cable set 120 (which connects links 110 and 114) while leaving cable set 118 (which connects links 108 and 112) without additional tension beyond baseline. In this case, links 110 and 114 are locked, while 108 and 112 are free to articulate.

FIGS. 27-34 show an embodiment of this invention that utilizes a friction-based locking mechanism. As in the above-described embodiments, articulatable tool 800 has an end effector 802 at its distal end and an end effector actuator 804 within a handle 806 at its proximal end. Tool 800 may be used in any of a variety of types of procedures, including for example, laparoscopic procedures that require grasping, cutting, or sealing within a patient; it could further be used percutaneously as a catheter, and in an embodiment that includes a flexible shaft, it could be used in endoscopic procedures.

Tool 800 has ball and socket links consisting of proximal active links 808 and 810 separated by a bushing 809. Proximal link 808 is connected to and moves with handle 806. A second proximal bushing 811 is disposed between link 810 and an articulation lock (described in more detail below) on the proximal end of the shaft 816. The bushings have convex surfaces interacting with corresponding concave surfaces on the links 808 and 810 and on the proximal end of the articulation lock. Likewise, distal active links 812 and 814 are separated by a bushing 813, and a second distal bushing 815 is disposed between the distal end of shaft 816 and active link 814. Distal link 812 is connected to and moves with end effector 802. Like their counterparts, spacer links 813 and 815 have convex surface on their ends which interact with corresponding concave surfaces on active links 812 and 814 and on the distal end of shaft 816. Sets of articulation cables 818 and 820 extend between the proximal and distal active links to control the articulation of the tool. Operation of end effector 802 may be as in the FIG. 1 embodiment, where movement of end effector actuator 804 moves rod 825 to open and close the end effector jaws. Further details of the types links suitable for use with this invention, such as ball and socket joints, and pivoting single-degree-of freedom joints, or any type of joint where friction affects the movement of links relative to each other, may be found in US 2005/0273084 US 2006/0111209, and US 2006/0111210.

Figure 29:
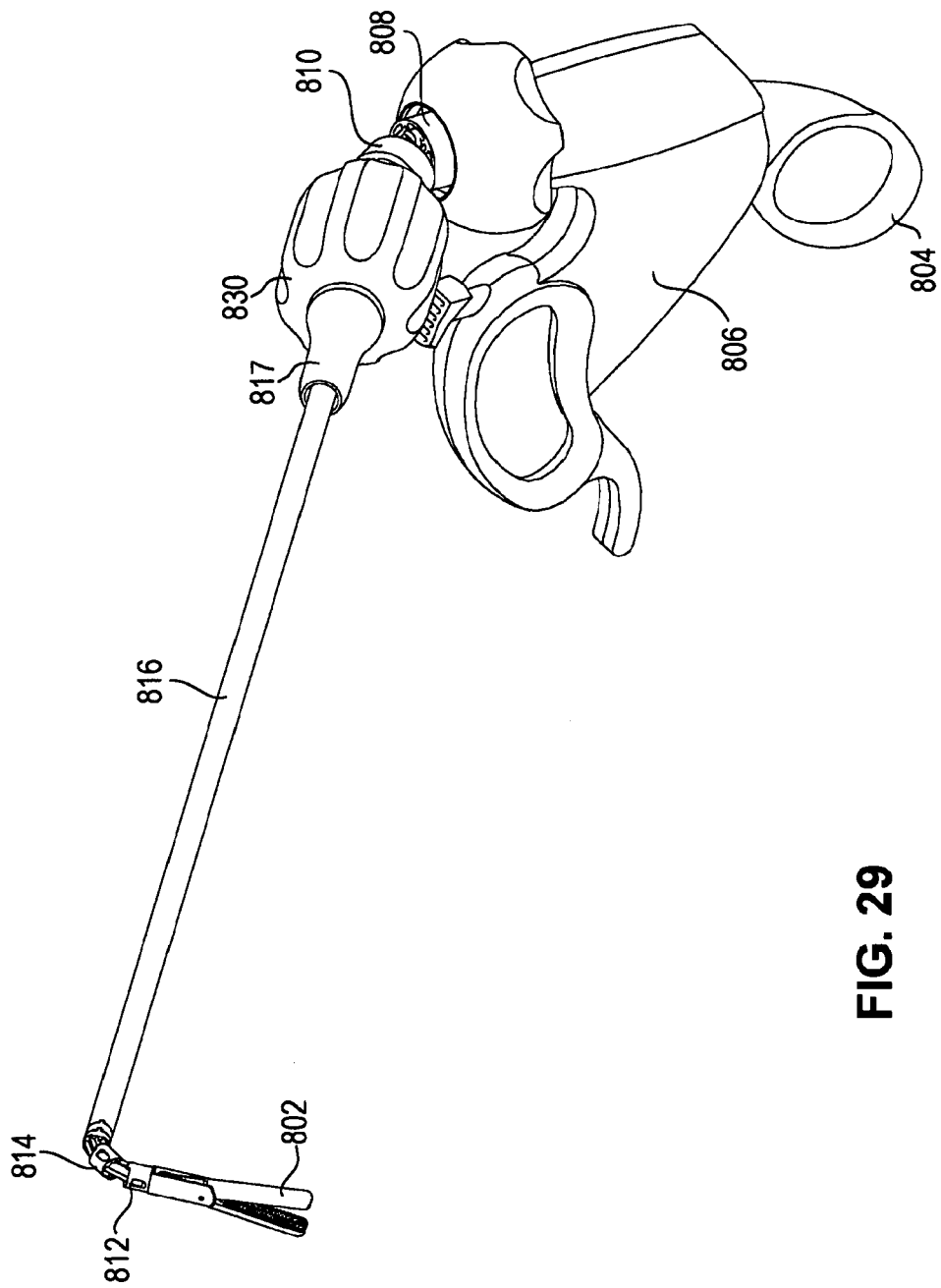
FIG. 29 is a perspective view of the tool shown in FIG. 27, the tool in an articulated position.
Figure 30:
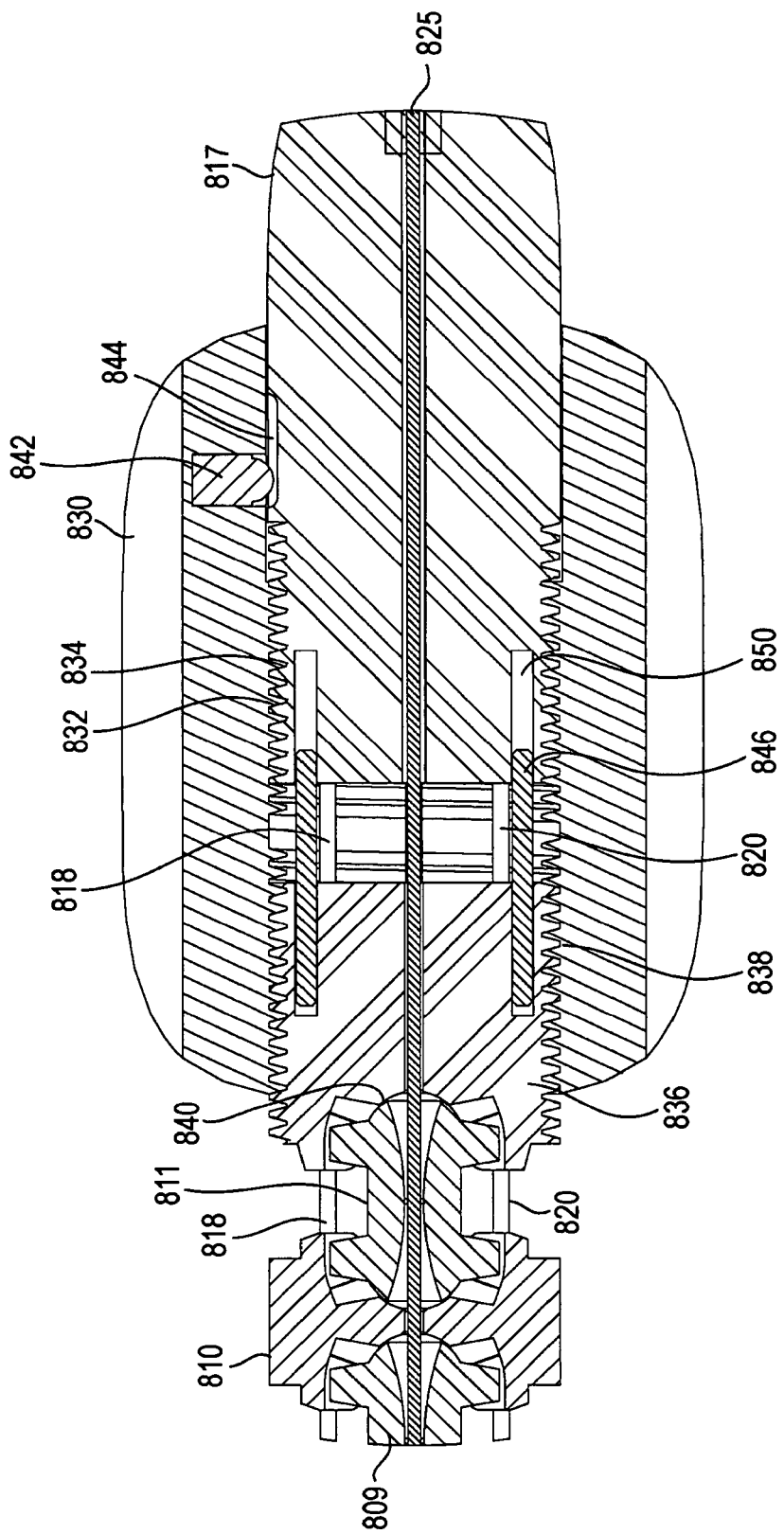
FIG. 30 is a cross sectional view of the cylindrical articulation lock depicted in FIGS. 27-34 showing the detail of the internal threaded portion with right hand and left hand threads that vary the tension on cables threaded through the links.
Figure 31:
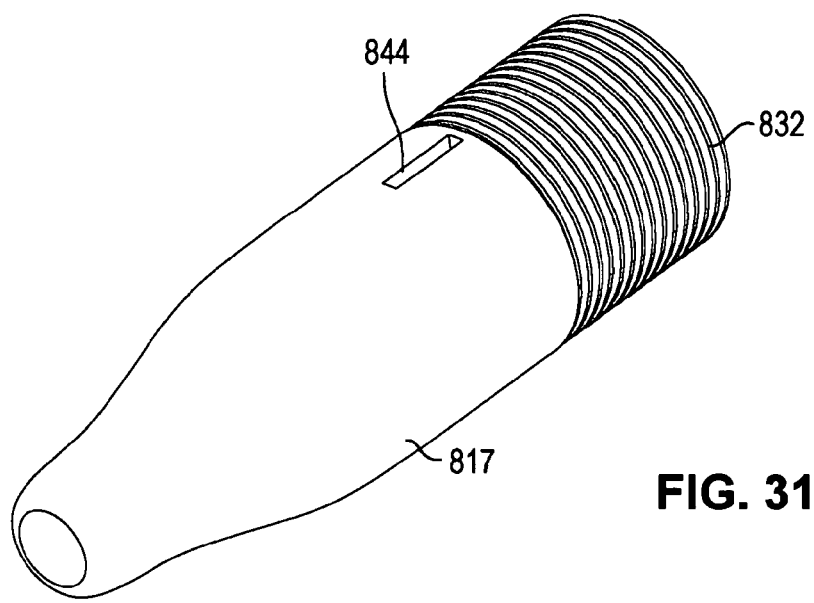
FIG. 31 is a member of a series extending through FIG. 34 showing details of components of the articulation lock.

As in the other embodiments, movement of handle 806 and proximal link 808 with respect to proximal link 810 moves end effector 802 and distal link 812 in a relative and corresponding manner. Likewise, movement of proximal link 810 with respect to shaft 816 moves distal link 814 with respect to shaft 816 in a relative and corresponding manner. This relative articulation movement provides a way for a user to remotely manipulate the end effector through movement of the handle, as shown in FIG. 29.

In order to maintain a particular position of the end effector with respect to the shaft, the articulating tool of this embodiment has an articulation lock. In this embodiment, the articulation lock is a mechanism that elongates the tool's shaft 816 with respect to the articulation cable sets, thereby applying tension to the ball and socket interfaces of the links. This interface tension provides sufficient friction to maintain the orientation of the links with respect to each other, thereby locking the articulating tool and preventing further articulation. It should be appreciated that the tool can be locked in a straight configuration (as shown in FIG. 27) or in a bent configuration (as shown in FIG. 29).

FIGS. 30-34 show details of the articulation lock of this embodiment. Right handed threads 832 are formed on the exterior of a shaft extension 817 on the proximal end of shaft 816. Surrounding the proximal end of shaft extension 817 is a cylindrical sleeve 830 having an internal threaded portion 834 with right handed threads corresponding to threads 832 on shaft extension 817. Also disposed within the bore of sleeve 830 is a threaded plug 836 with left handed threads corresponding to a second internal threaded portion 838 of sleeve 830 that also has left handed threads. The proximal end of plug 836 has a concave bearing surface 840 that interacts with the convex bearing surface of bushing 811.

In its unlocked position, the articulation lock of this embodiment is rotated clockwise to a position in which the cable sets 818 and 820 are slack enough to permit the active and spacer links to move with respect to each other. To lock or prevent articulation, sleeve 830 is rotated counterclockwise, thereby moving plug 836 and shaft extension 817 away from each other. This elongation of the effective length of the tool applies tension to the cables and forces the convex and concave bearing surfaces of the bushings and links against each other. The friction caused by this tight engagement locks the tool in its articulated position.

Figure 32:
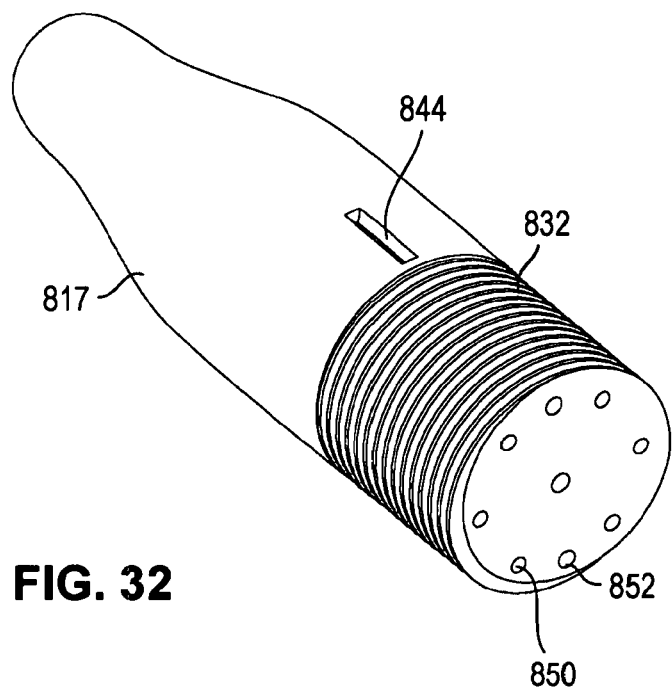
Figure 34:
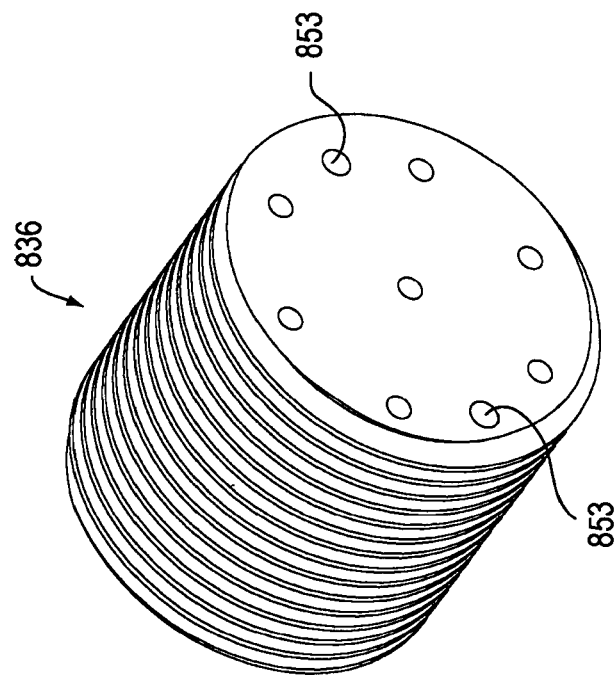
Figure 33:
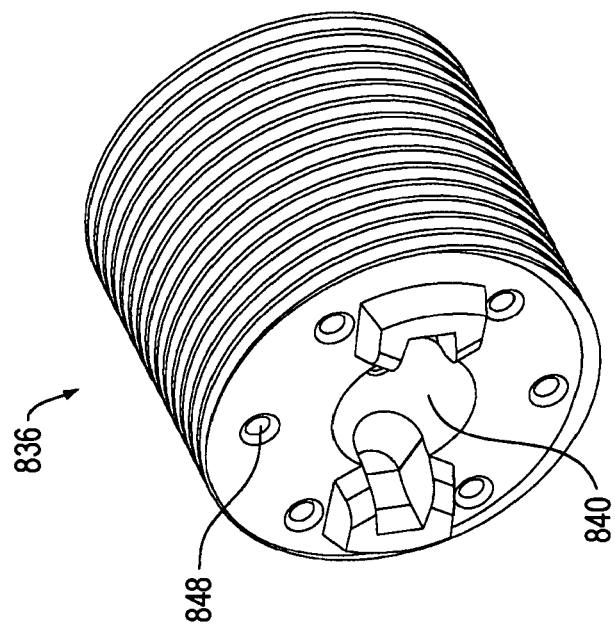
FIG. 33 shows the threaded plug portion of the articulation lock, configured within the proximal portion of the articulation lock, from a distal-looking perspective, showing left hand threads, and proximal facing concave bearing surface.

Ball plunger 842 extends radially inward from sleeve 830 and acts as a detent by extending into a slot 84, a slot that the ball plunger hits at different axial locations. The slot takes the place of a single hole for the ball of the ball plunger to fall into. In this way, the ball plunger and a single slot can form multiple stop detents at each 360 degree rotation of the sleeve 830. Multiple ball plungers and slots can be used to increase the resolution of the detents. Counter torque pins 846 are disposed in corresponding holes in the plug and shaft extension, respectively. These pins keep the shaft extension 817 and the plug 836 at the same angular orientation and allow the two components to translate axially with respect to each other when the sleeve 830 is rotated. Further details of the articulation lock are shown in FIGS. 31-34. FIG. 32 shows lumens 850 to permit cable sets 818 and 820 to pass through the shaft extension. Hole 852 (FIG. 32) is the hole that counter torque pins 846 ride in (this hole and the one 180 degrees from it), and FIG. 34 shows lumens 848 to permit cable sets 818 and 820 to pass through the plug 836 Holes 853 In (FIG. 34) accept the counter torque pins. Call it holes 848 (FIG. 33) are for articulation cables.

Figure 35:
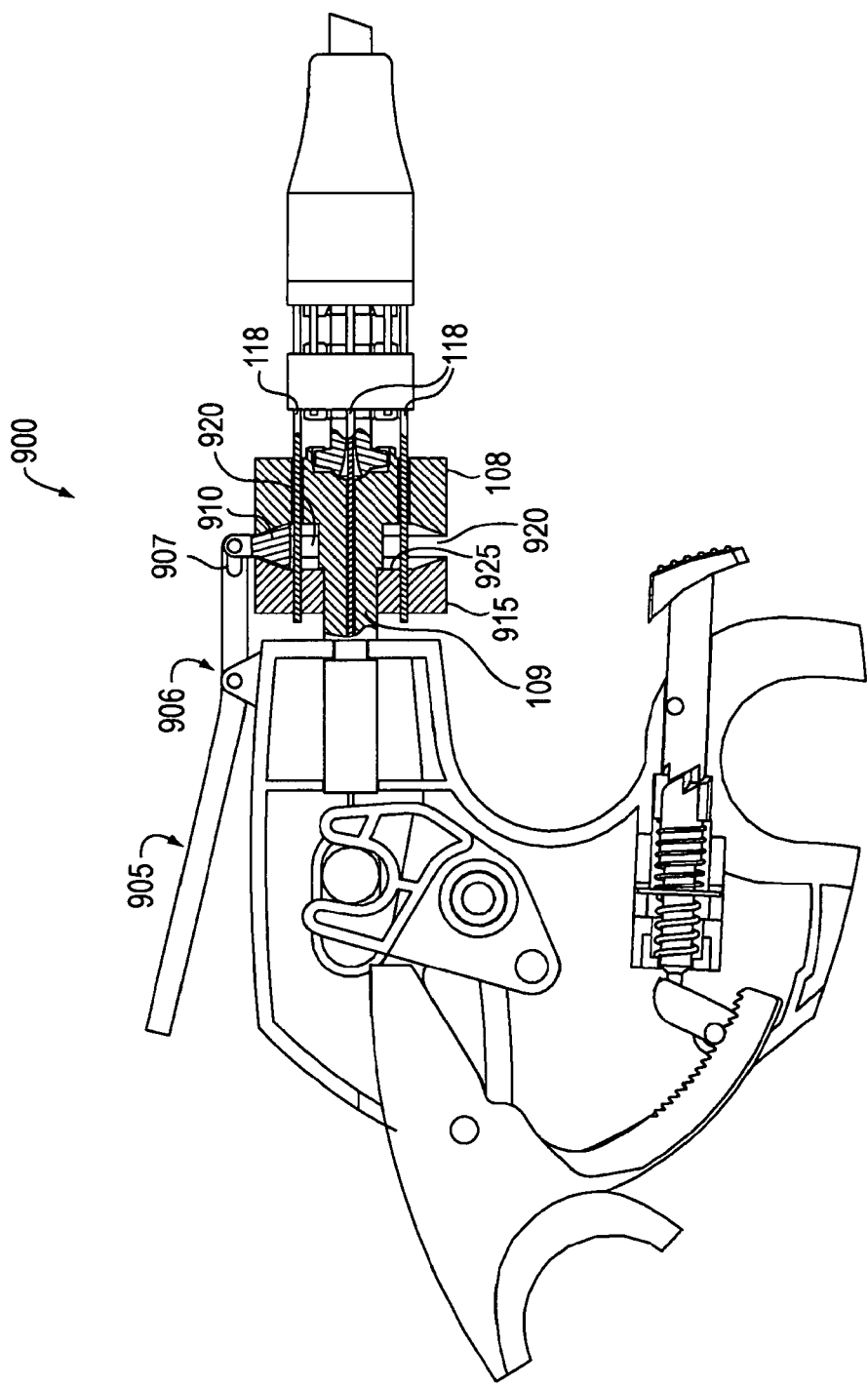
FIG. 35 is a side exposed view of the proximal portion of a tool with an articulation lock comprising a locking lever and wedge that is located proximal to the most proximal links. This articulation lock embodiment is of a type that adjusts tension on the tension bearing members that connect articulating links, thereby increasing friction between links. The lever shown in an unlocked position.
Figure 36:
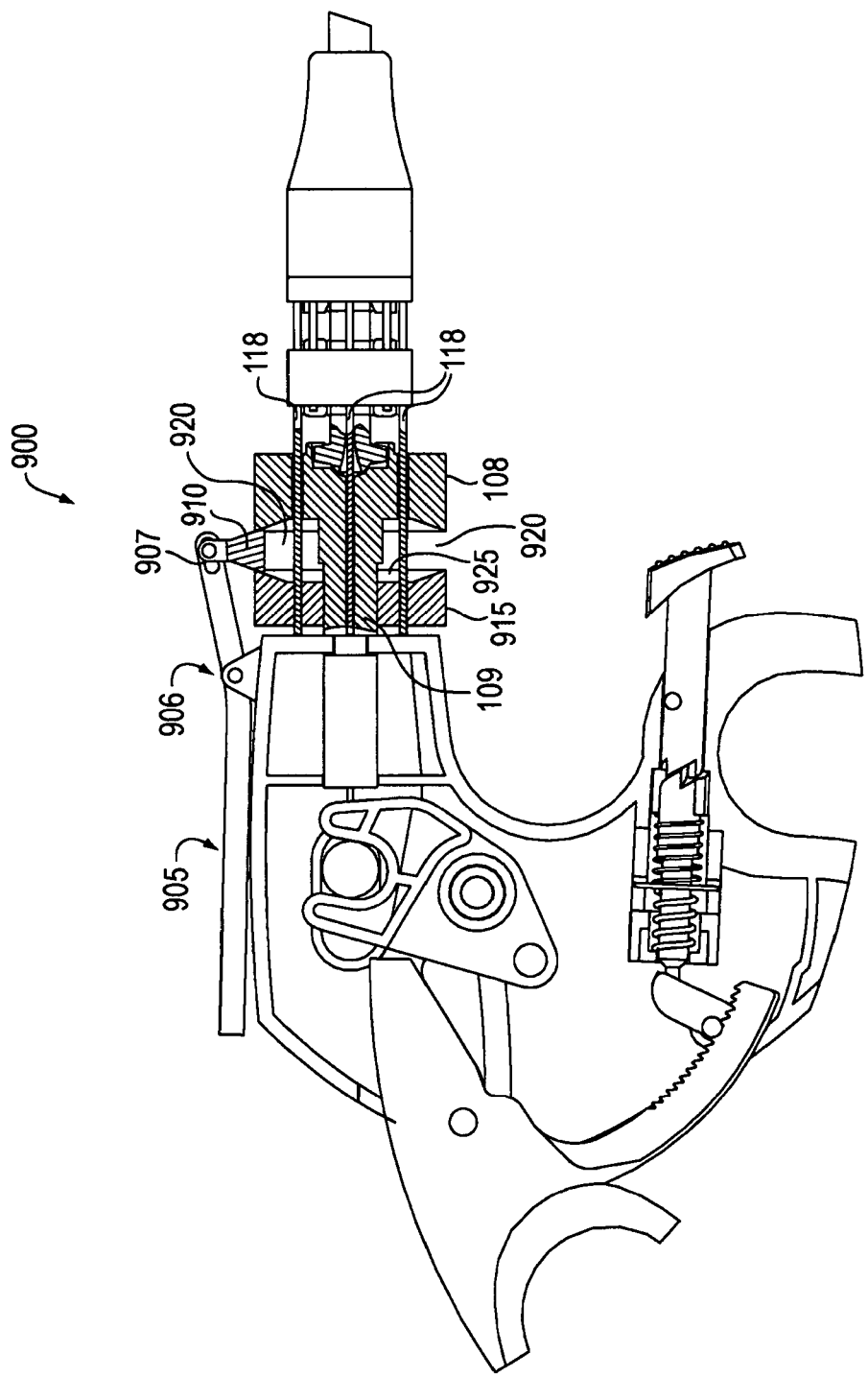
FIG. 36 shows the articulation lock mechanism depicted in FIG. 35, but in a locked position, to prevent articulation.

FIG. 35 is a side exposed view of the proximal portion of a tool 900 with an articulation lock comprising a locking lever 905 and locking wedge 910 fitted into a circular locking groove 920 with ramped surfaces. The groove 920 is formed from the proximal face of proximal link 108 and the distal face of a locking disc 915. Cables of cable set 118 go through oversize holes in link 108 and are anchored in locking disc 915. This articulation lock embodiment is of a type that adjusts tension on the cables that connect articulating links, thereby increasing friction between links. The lever 905 is shown in an unlocked position. FIG. 36 shows the articulation lock mechanism depicted in FIG. 35, but in a locked position, to prevent articulation.

Locking wedge 910 is narrow at its point of attachment to the lever 905, flaring outward from its base. Locking groove 920 is wide at its radial base, and narrows as it progresses radially outward. The sloping proximal and distal walls of the groove may be considered ramps; the angles of the ramps complement the angles of the proximal- and distal-facing surfaces of the wedge 910. Locking disc 915 encircles a proximally-projecting spindle portion 109 of link 108, and is slidable on that portion. Locking disc 915 is pulled or biased distally by the tension of cables 118, its distal movement is stopped by a shoulder 925 on the proximal face of link 108. The effect of the action of the locking lever is to pull the locking wedge 910 radially outward of groove 920; in so doing, the wedge 910 pushes the locking disc 915 proximally. As the disc 915 is pushed proximally, it pulls on the cables of cable set 118, thereby increasing their tension. By this action, the articulation lock is locked. This locking action is variable, according to the degree to which the wedge is pulled out of its groove.

In FIGS. 35 and 36, the locking lever 905 is bent at the point of pivotable connection 906. A slot 907 accommodates the linkage to the base of locking wedge 910. The slot is sufficiently wide to accommodate movement of wedge distally and proximally, as it moves according to the relative proximal-distal position of the wedge. The locking lever 905 depicted here is a mere example of any number of mechanisms that could controllably and reversibly move the wedge 910. The lever as depicted has no tine to fix the locking lever in any position, but many mechanisms are known to fix the position of the lock. A ratchet mechanism, for example, could provide a variable level of locking tension in the cables, such that the mechanism could be fixed in a malleable condition. In another variation, the angle of the locking wedge 910 could be shallow enough such that the locking mechanism, when locked, stays in place due to friction between the locking wedge 910 and the walls of the grove 920. In other words, the angle between the mating components could be shallow enough that the tension in the cables could not back-drive the mechanism. In this case, the locking lever 905 would need to be pushed upward to unlock the mechanism.

Figure 37:
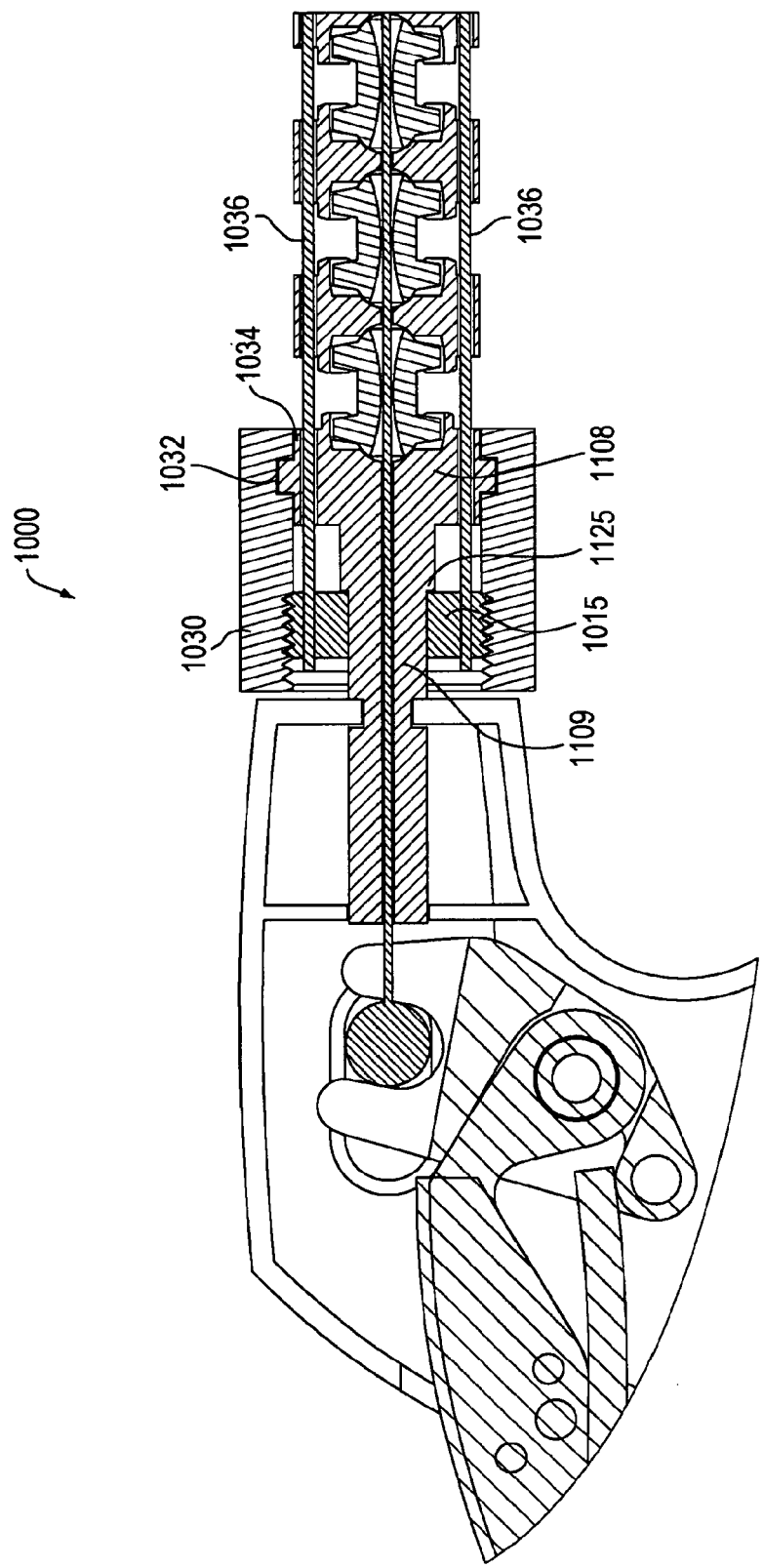
FIG. 37 is a side exposed view of the proximal portion of a tool with an articulation lock mechanism comprising a cylindrical locking sleeve with a translating locking disc connected to tension bearing members. The mechanism is located proximal to the most proximal links. This articulation lock embodiment is of a type that adjusts tension on tension bearing members that connect articulating links, thereby increasing friction between links. The mechanism is shown in an unlocked position.

FIG. 37 is a side exposed view of the proximal portion of a tool 1000 with an articulation lock mechanism comprising a cylindrical locking sleeve 1030 with a translating locking disc 1015 connected to tension bearing members. This articulation lock embodiment is of a type that adjusts tension on tension bearing members that connect articulating links, thereby increasing friction between links. Locking sleeve 1030 is rotatable around proximal link 1108; the sleeve has an internal threaded portion which mates with external threads of locking disc 1015, moving the disc proximally and distally depending on the direction the locking sleeve is turned. Locking disc 1015 encircles a proximally-projecting spindle portion 1109 of link 108, and is slidable on that portion. Locking disc 10515 is pulled or biased distally by the tension of cables 1036, its distal movement is stopped by a shoulder 1125 on the proximal face of link 1108. A slot 1032 in the sleeve mates with a flange 1034 in link 1108 to prevent translating movement either proximally or distally, as the sleeve is rotated. As the proximal-distal position of the sleeve is thus fixed, rotational translation force is imparted to the locking disc 1015, which due to its connection to the cables 1036, thereby adjusts the tension on the cables. Counter torque pins (not shown) similar to counter torque pins 818 in FIG. 30 could be provided to prevent the locking disk 1015 from rotating when the locking sleeve 1030 is rotated.

Figure 38:
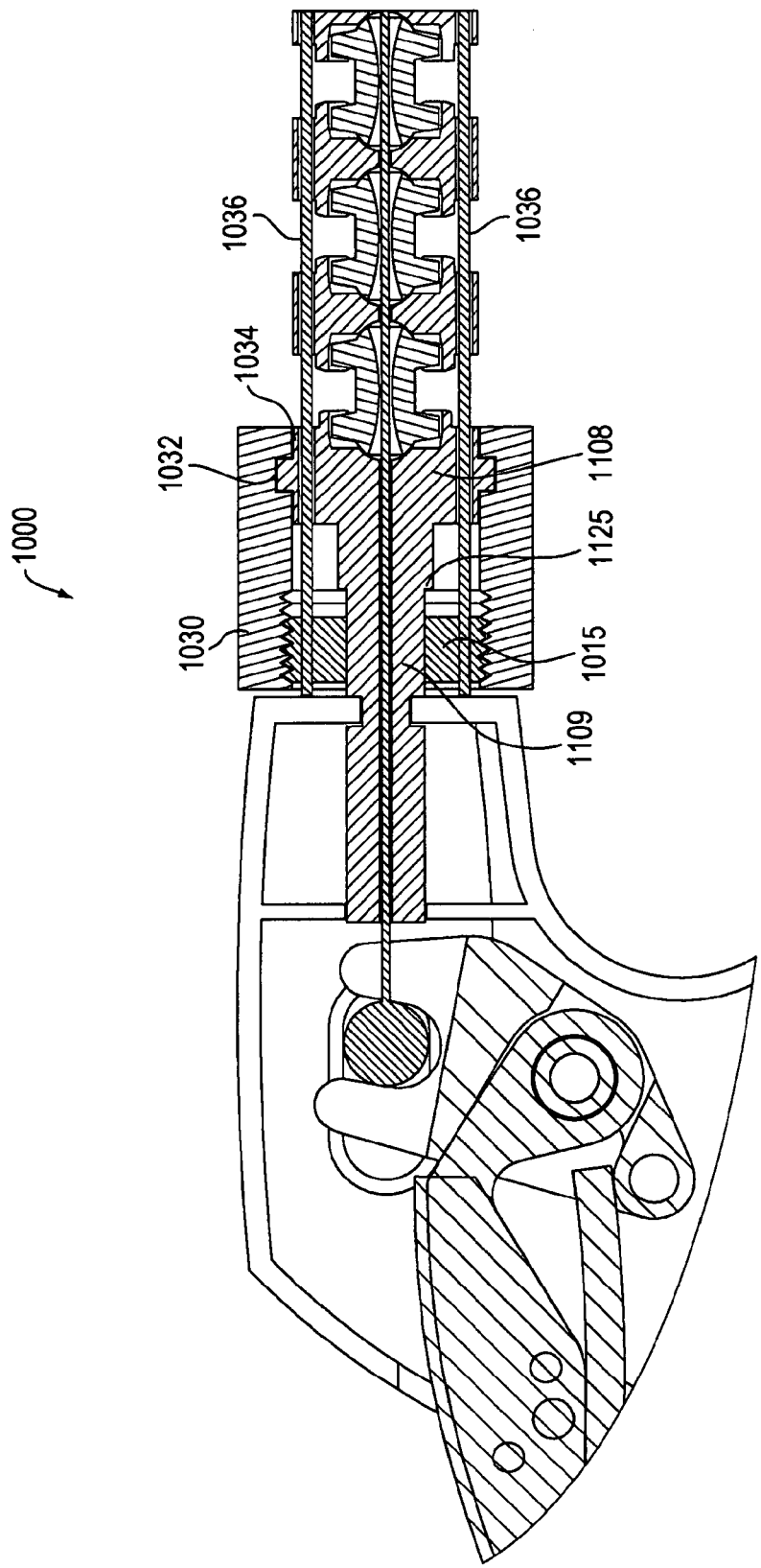
FIG. 38 shows the articulation lock mechanism depicted in FIG. 37, but in a locked position, to prevent articulation.

The mechanism is shown in an unlocked position in FIG. 37, and in locked position in FIG. 38, where the locking disc 1015 can be seen to have moved to a more proximal position. By moving proximally with the cables attached, the cables have thus accumulated a higher level of tension.

The particular embodiment shown in FIGS. 37 and 38 shows a set of three proximal links and a single set of cables. This number of links and number of cable sets is only an example of combinations of links and cable sets to which friction based articulation locking mechanisms, per embodiments described herein may be applied. Articulation locks of all types described herein may be applied to embodiments without limitation to the number of links and without regard to the number of cable sets, connecting the links, nor to the number of cables in the sets. Further, articulation locks that are friction-based, can be applied to any articulating mechanism that makes use of links whereby an increase in the tension of cables connecting the links causes an increase in friction as the surfaces of articulating links as they move relative to or across each other.

Figure 39:
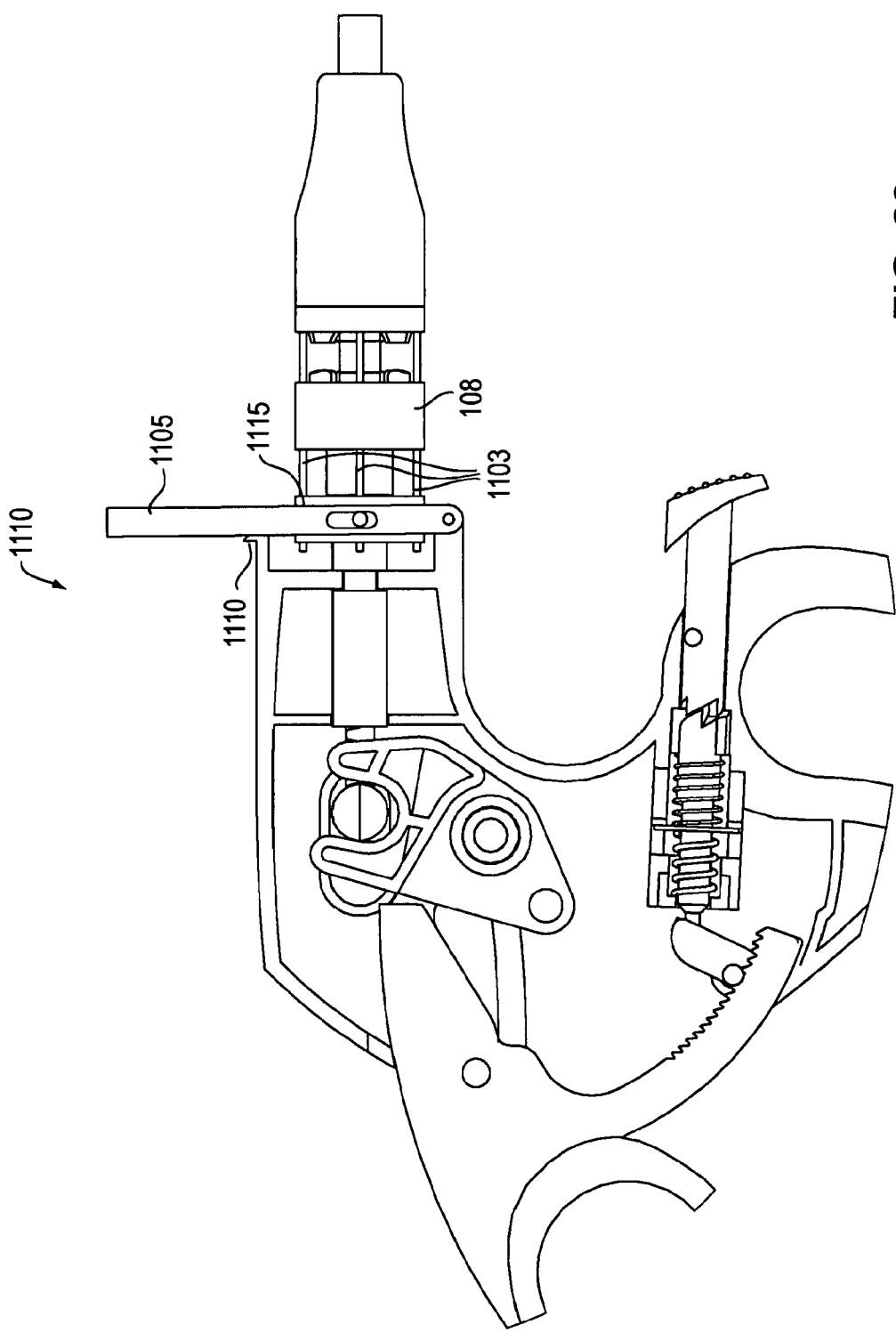
FIG. 39 is a side exposed view of the proximal portion of a tool with an articulation lock comprising a locking mechanism comprising a disc with a lever, the mechanism located proximal to the proximal link. This particular embodiment has only one pair of links and one set of tension bearing members. This articulation lock embodiment is of a type that adjusts tension on tension bearing members that connect articulating links, thereby increasing friction between links. The mechanism is shown in an unlocked position.

FIG. 39 is an exposed side view of the proximal portion of a tool 1100 with an articulation lock comprising a locking mechanism comprising a locking disc 1115 and with a side-mounted locking lever 1105, the mechanism located proximal to the proximal link This particular embodiment has only one pair of links and one set of tension bearing members. As with the previously described embodiment the cables 1103 of the cable set slip through proximal link 108 and terminate in the locking disk 1115. Adjusting the relative proximal-distal position of the locking disc through the action of the lever 1105, thus adjusts tension on the cables. A tine 1110 on the handle secures the lever in the locked position (compare FIGS. 39 and 40). The tine 1110 is but one of many mechanisms that could secure such a lever, other embodiments include, for example, a rack of teeth such that the lever could be held at various positions, thereby creating various levels of tension in the cables, and thereby, in a mid-position, fixing the articulation mechanism in a malleable state.

Figure 40:
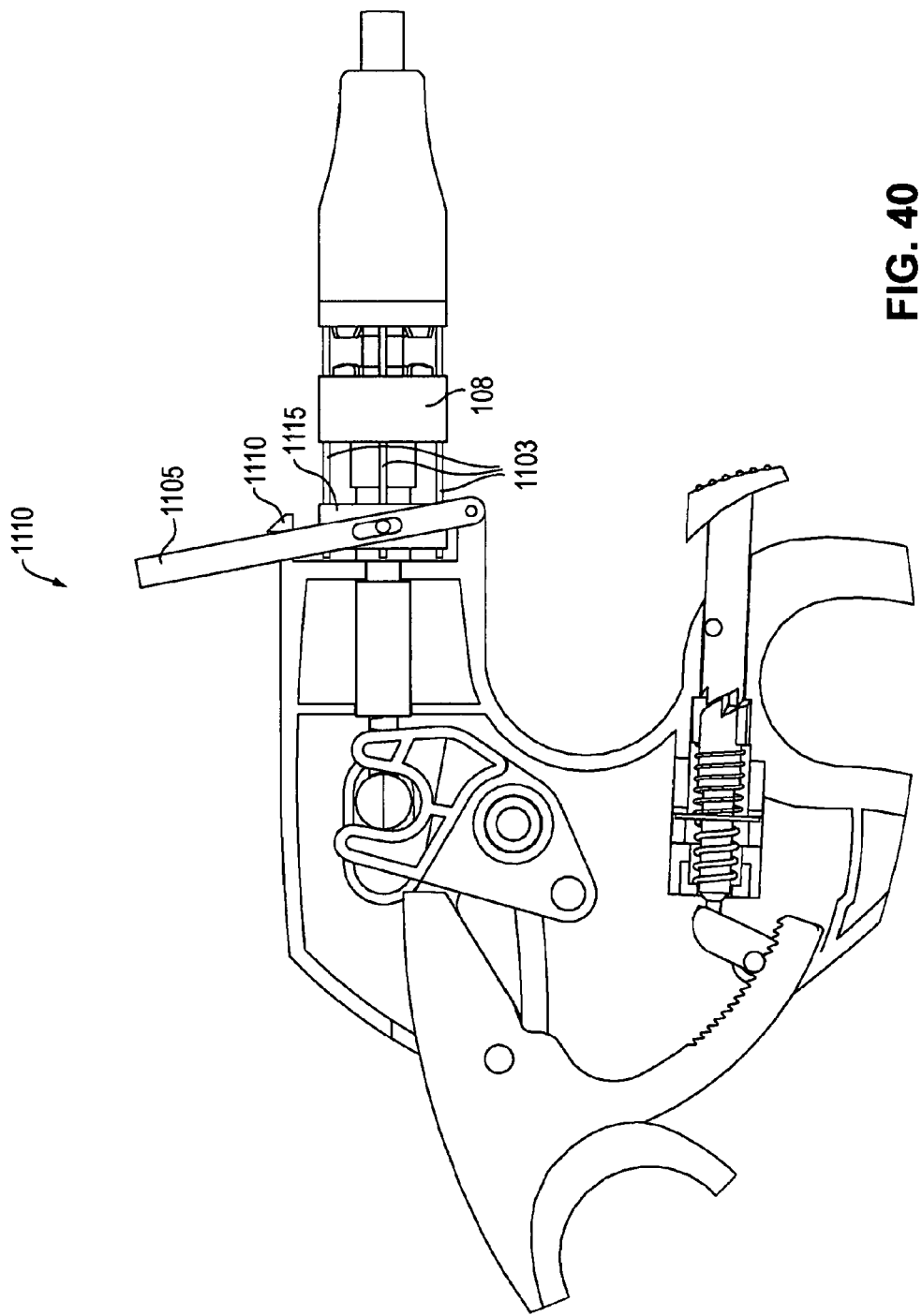
FIG. 40 shows the articulation lock mechanism depicted in FIG. 39, but in a locked position, to prevent articulation.

The mechanism of FIG. 39 is shown in an unlocked position. FIG. 40 shows the articulation lock mechanism depicted in FIG. 39, but in a locked position, to prevent articulation. In terms of the nature of this embodiment in general terms, this articulation lock embodiment is of a type that adjusts tension on tension bearing members that connect articulating links, thereby adjusting the amount of friction between links. In some embodiments, a locking disc (like disc 115) can be integrated into a link 110 (see FIGS. 1-4 for reference). In such a configuration inner links 110 and 114 can be locked, while outer links 108 and 112 remain free to articulate.

FIG. 41 is a side view of a tool 1100 with cam-based articulation locking mechanism that is located between proximal and distal links. This articulation lock embodiment is of a general type that adjusts tension on the tension bearing members that connect articulating links, thereby increasing friction between links. In this embodiment, the link tension is adjusted by varying the effective length of the shaft, and more specifically, shaft length is varied by a cam mechanism 1210. The lever is shown in an unlocked position, thereby allowing articulation.

FIG. 42 is a detail view of the cam lock of FIG. 41. (42A) a locked position, and (42B) an unlocked position. The detailed views of FIG. 42 emphasize the difference in relative location of the telescoping shaft components in the two positions. FIG. 42 provides a detail of cam mechanism 1210, which comprises three main components, a cam lever 1212, an inner shaft component 1214, and an outer telescoping shaft component 1215. The cam lever 1212 comprises a cam surface 1213 that rotates across the surface of flange 1216, a portion of the inner telescoping shaft component 1214. As the cam lever 1212 moves from an unlocked position to a locked position, the camming action forces the outer telescoping shaft component 1215 forward with respect to the inner shaft component 1214, thereby lengthening the shaft. While the length of the shaft increases, the distance between the termination points of the cables in the links at the proximal and distal ends of the articulating mechanism increases, thereby increasing tension on the cables. As described above, increased tension in the cables is distributed through the length of the cable, increasing the friction associated with movement across the abutting surfaces of links on the proximal and distal ends of the articulating mechanism. Such friction impedes link-link movement to a degree that varies between converting free movement to malleable movement, to a seizure that substantially prevents movement.

Figures 43A, 43B:
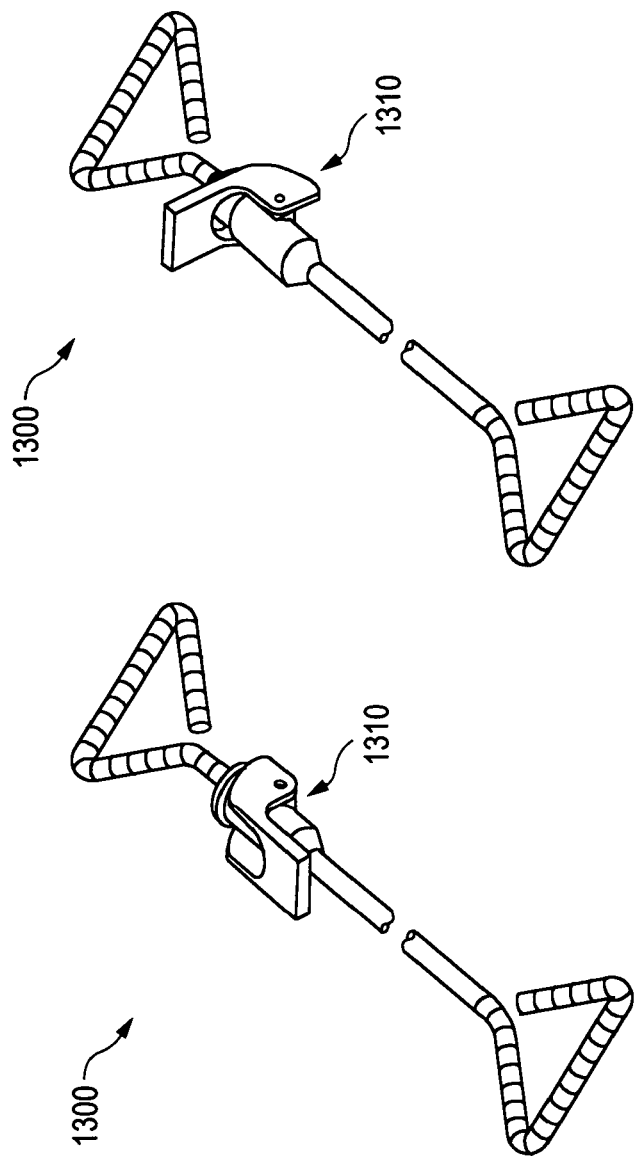
FIGS. 43A and 43B provide perspective views of an articulating mechanism configured as a liver retractor, with a cam-based articulation locking mechanism that is located between proximal and distal links.

FIG. 43 is a perspective view of tool 1300 with an articulating mechanism configured as a liver retractor, with a cam-based articulation locking mechanism 1310 that is located between proximal and distal links: 43A shows the locking mechanism in the unlocked position; 43B shows the locking mechanism in the locked position. The locking mechanism and its operation are substantially the same as described in the preceding embodiment. This embodiment has no other specific end effector; the mechanism itself serves as the engaging portion of the tool. This embodiment provides an example of a tool wherein the articulating mechanism itself, to which the inventive articulation lock is applied, is the functional portion of the tool, not a dedicated end effector Embodiments of the articulation locks disclosed in this present application may thus be appropriately fitted into devices such as the one shown in FIG. 43 as well as into many other similar devices such as those disclosed in detail in U.S. Pat. No. 7,090,637 which is hereby incorporated by this reference.

Figure 44:
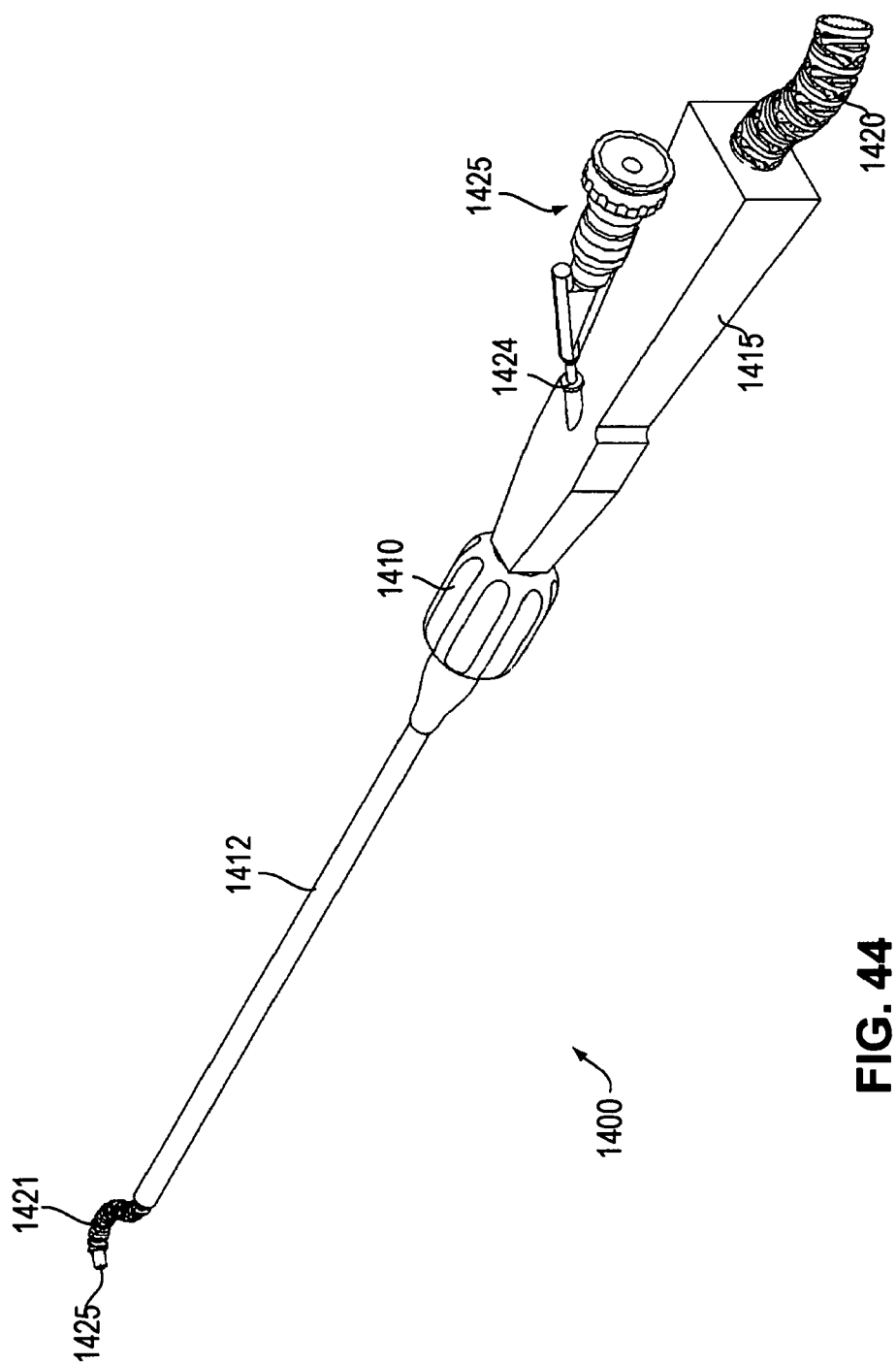
FIG. 44 is a perspective view of an articulating sheath device with an articulation lock in the form of a cylindrical sleeve comprising an internal threaded portion (not shown in this surface view) located between proximal and distal links. This articulation lock embodiment is of a type that adjusts tension on the tension bearing members that connect articulating links, thereby increasing friction between links.

FIG. 44 is a perspective view of an articulating sheath device 1400 with an articulation lock in the form of a cylindrical rotating sleeve mechanism 1410 comprising an internal threaded portion (not shown in this surface view) located between proximal and distal links. This type of device can make use of any of the articulation lock embodiments described herein; the particular embodiment described herein is provided by way of example as to how such locks may be applied. This articulation lock embodiment is of a type that adjusts tension on the tension bearing members that connect articulating links, in this embodiment it increases tension by making the shaft 1412 longer, thereby increasing friction between links. In the embodiment depicted, the shaft 1412 is rigid, but in other embodiments it may be flexible. The proximal portion of the device 1400 comprises a handle 1415, and emerging from the proximal portion of the handle is a set of proximal links 1420 that correspond to a distal set of articulating links 1421, emerging from the shaft 1412. The handle further comprises an entry port 1424 for a flexible endoscopic tool or flexible endoscope 1425, which is shown in the figure adjacent to the entry port 1424 and also emerging from the distal portion of the articulating sheath. The articulating links 1420 and 1421 are shown in greater detail in FIGS. 45 and 46, and described further below.

Embodiments of the inventive friction-based articulation locks described herein may be applied to articulating mechanisms that utilize any type of link that has a surface-to-surface relative motion with a neighboring link. Ball and socket type links represent one example; other types of links appropriate for embodiments of the articulation lock mechanism described herein include U.S. published patent applications. US2005/0273084, US2006/0111616, US2006/0111209, and US2006/0111210, all of which are hereby incorporated by this reference.

FIG. 45 shows a set of pivoting-hinge type links 1500. In (45A) the top two links are in pivoted in an articulated configuration, each one tipped at a hinge point where it has a single degree of freedom, and in (45B) all links are in a straight, unarticulated position. FIG. 45 shows a series of cable holes 1505 arrayed around the circumference of the rim of the link, and a large central bore 1510 The radial central bore can accommodate other instruments, or components of an instrument that control an end effector, or for electrical wires, or for lasers or fiber optical instruments. These pivoting-hinge type links are similar to the flex-hinge type of links described in U.S. patent application Ser. No. 10/948,911, except for differences in specifics of the hinge (pivoting vs. flex). These pivoting hinge joints have one degree of freedom, and thereby differ from ball and socket joints, which have two degrees of freedom.

Important for the articulation locking is that each link is connected to its adjacent link by a connection whose movement can be impeded by an axial load applied by increasing tension in the cables on which the links are strung. The impeding of movement can be either of a modest type, in which the link movement becomes malleable, creating a mechanism as a whole that is malleable, or the movement can be substantially blocked or seized up when a sufficient axial load is applied. When movement of links is substantially prevented, the mechanism as a whole becomes locked in configuration, whether the mechanism is straight or articulated.

While the inventive surgical instruments and devices have been described in some detail by way of illustration, such illustration is for purposes of clarity of understanding only. It will be readily apparent to those of ordinary skill and in the art in light of the teachings herein that certain changes and modifications may be made thereto without departing from the spirit and scope of the appended claims. For example, while the articulation mechanism and articulation lock embodiments described in here have typically been in the context of tools with an articulating mechanism comprising at least two links, the mechanisms may be used in an instrument comprising only a single link, a multiplicity of links, and with any number of cables or cable sets operably connecting the links. Further, the articulating mechanisms may be used in the absence of many features commonly associated with some articulatable instruments, such as handles, shafts, rotatability features, and dedicated end effectors. Finally, while the context of the invention is considered to be surgical or medical diagnostic procedures, the articulation locking mechanisms or tool having such mechanisms may have utility in other non-medical contexts as well.

What is claimed is:

1. A tool comprising:
a distal portion and a proximal portion spaced apart by a shaft along a longitudinal axis, the distal portion including a plurality of distal links and the proximal portion including a plurality of proximal links, wherein the plurality of distal and proximal links are configured to form multiple pairs of links, each pair comprising a proximal link and a corresponding distal link;
multiple sets of tension load bearing members, each set connecting the proximal link and the corresponding distal link of one of the multiple pairs of links and terminating at the links of the pair to transfer movement therebetween; and
an articulation lock positioned between the distal portion and the proximal portion and configured to allow passage of each set of tension load bearing members through the articulation lock, and to increase an effective length of the shaft to force adjacent distal links into frictional engagement and adjacent proximal links into frictional engagement to impede movement of the distal and proximal portions.

2. The tool of claim 1, further comprising a handle with an end effector actuator disposed at the proximal portion, such that moving the end effector actuator causes movement of a proximal link of the plurality of proximal links.

3. The tool of claim 1, further comprising:
an end effector disposed at the distal portion; and
an end effector actuator disposed at the proximal portion, wherein movement of a distal link of the plurality of distal links causes angular movement of the end effector with respect to the shaft.

4. The tool of claim 1, wherein the articulation lock comprises a tension adjusting mechanism configured to vary the effective length of the shaft to vary tension in a set of the tension load bearing members to vary friction between adjacent links among the plurality of proximal links.

5. The tool of claim 1, wherein the articulation lock is configured to maintain a first configuration of the distal and proximal links when the distal and proximal links are in the first configuration when the articulation lock is engaged.

6. The tool of claim 1, wherein the articulation lock has a partially engaged state wherein a tension on the tension load bearing members is such that movement between adjacent links is partially impeded and the articulation mechanism as a whole is malleable.

7. The tool of claim 1, wherein tension on the tension load bearing members is such that movement of adjacent links is substantially blocked when the articulation lock is in an engaged state.

8. The tool of claim 1, wherein the articulation lock comprises a tension adjusting mechanism configured to vary the effective length of the shaft, the tension adjusting mechanism including:
a sleeve featuring a first threaded portion with right hand threads and a second threaded portion with left hand threads,
a first threaded element featuring right hand threads, and
a second threaded element featuring left hand threads.

9. The tool of claim 1, wherein the articulation lock comprises a lever mechanism configured to vary the effective length of the shaft disposed between the distal portion and the proximal portion.

10. The tool of claim 1, wherein the tension load bearing members comprise a set of cables.

11. The tool of claim 1, wherein the articulation lock comprises a tension adjusting mechanism including a proximal component and a distal component.

12. The tool of claim 11, wherein an engaged state of the articulation lock results in increasing the effective length of the shaft by moving the proximal component of the tension adjusting mechanism and the distal component of the tension adjusting mechanism away from each other.

13. The tool of claim 12, wherein friction between the adjacent links is increased when the effective length of the shaft disposed between the proximal portion of the tool and the distal portion is increased.

14. A tool, comprising:
a distal portion and a proximal portion spaced apart by an effective distance, the distal portion including first and second distal links and the proximal portion including first and second proximal links;
a tension load bearing member configured to connect the first proximal link to the first distal link, and to transfer movement therebetween; and
an articulation lock configured to increase the effective distance between the distal portion and the proximal portion to increase friction between the first and second proximal links, wherein the articulation lock is configured to allow passage of the tension load bearing member through the articulation lock.

15. The tool of claim 14, wherein the articulation lock comprises a tension adjusting mechanism including a first component and a second component, the tension adjusting mechanism configured to vary the effective distance by varying a distance between the first component and the second component.

16. The tool of claim 15, wherein the first component and the second component are engaged in a threaded configuration to allow varying of the distance between the first component and the second component.

17. The tool of claim 16, wherein the articulation lock is configured to vary friction between the first and second proximal links by varying the effective distance between the distal portion and the proximal portion.

* * * * *

UNITED STATES PATENT AND TRADEMARK OFFICE
CERTIFICATE OF CORRECTION

PATENT NO. : 9,737,365 B2
APPLICATION NO. : 14/735564
DATED : August 22, 2017
INVENTOR(S) : David Elias Hegeman et al.

It is certified that error appears in the above-identified patent and that said Letters Patent is hereby corrected as shown below:

In the Specification

In Column 1, Line 16: delete "This application"

Signed and Sealed this
First Day of May, 2018

Andrei Iancu
*Director of the United States Patent and Trademark Office*